US009885689B2

(12) United States Patent
Tanaka

(10) Patent No.: US 9,885,689 B2
(45) Date of Patent: Feb. 6, 2018

(54) SENSOR APPARATUS

(71) Applicant: KYOCERA CORPORATION, Kyoto (JP)

(72) Inventor: Hiroyasu Tanaka, Kyoto (JP)

(73) Assignee: KYOCERA CORPORATION, Kyoto (JP)

( * ) Notice: Subject to any disclaimer, the term of this patent is extended or adjusted under 35 U.S.C. 154(b) by 63 days.

(21) Appl. No.: 15/035,174

(22) PCT Filed: Sep. 22, 2014

(86) PCT No.: PCT/JP2014/075065
§ 371 (c)(1),
(2) Date: May 6, 2016

(87) PCT Pub. No.: WO2015/079789
PCT Pub. Date: Jun. 4, 2015

(65) Prior Publication Data
US 2016/0290967 A1    Oct. 6, 2016

(30) Foreign Application Priority Data

Nov. 29, 2013    (JP) .................................. 2013-247447

(51) Int. Cl.
*G01N 29/22*    (2006.01)
*G01N 29/02*    (2006.01)

(52) U.S. Cl.
CPC ......... *G01N 29/022* (2013.01); *G01N 29/222* (2013.01); *G01N 2291/0423* (2013.01)

(58) Field of Classification Search
CPC ............... G01N 29/022; G01N 29/222; G01N 2291/0423

(Continued)

(56) References Cited

U.S. PATENT DOCUMENTS

| 5,130,257 A | 7/1992 | Baer et al. |
| 5,283,037 A | 2/1994 | Baer et al. |

(Continued)

FOREIGN PATENT DOCUMENTS

| JP | A 5-240762 | 9/1993 |
| JP | A 2005-249491 | 9/2005 |

(Continued)

OTHER PUBLICATIONS

International Search Report in International Application No. PCT/JP2014/075065, dated Dec. 22, 2014, in 1 page.

*Primary Examiner* — J M Saint Surin
(74) *Attorney, Agent, or Firm* — Duane Morris LLP

(57) ABSTRACT

A sensor includes an inflow section into which an analyte liquid flows; a first cover member; a detection element including an element substrate located on an upper surface of the first cover member, and a detection section which is located on an upper surface of the element substrate and is configured to detect a target contained in an analyte liquid; an intermediate cover member including a first upstream portion; a second cover member including a second upstream portion; and a flow channel which is surrounded by the intermediate cover member and the second cover member, is continuous with the inflow section, and extends at least to the detection section. A contact angle θ2a of a lower surface of the second upstream portion of the second cover member with the analyte liquid is smaller than a contact angle θ3 of an upper surface of the detection element with the analyte liquid.

17 Claims, 15 Drawing Sheets

(58) Field of Classification Search
USPC .......................................................... 73/61.7
See application file for complete search history.

(56) References Cited

U.S. PATENT DOCUMENTS

| | | | |
|---|---|---|---|
| 5,306,644 | A | 4/1994 | Myerholtz et al. |
| 6,235,488 | B1 | 5/2001 | Tom-Moy et al. |
| 9,772,310 | B2 * | 9/2017 | Fukuura ................. G01N 29/02 |
| 2002/0192718 | A1 | 12/2002 | Tom-Moy et al. |
| 2005/0239194 | A1 | 10/2005 | Takahashi et al. |
| 2014/0224002 | A1 | 8/2014 | Fukuura et al. |
| 2015/0263698 | A1 * | 9/2015 | Tanaka ............... H03H 9/02622 |
| | | | 310/313 C |
| 2017/0199180 | A1 * | 7/2017 | Kobayashi ........... G01N 29/022 |
| 2017/0227503 | A1 * | 8/2017 | Kobayashi ......... G01N 29/2462 |
| 2017/0261470 | A1 * | 9/2017 | Kobayashi ............. G01N 29/24 |

FOREIGN PATENT DOCUMENTS

| | | |
|---|---|---|
| JP | A 2006-162318 | 6/2006 |
| JP | A 2006-184011 | 7/2006 |
| JP | A 2010-239477 | 10/2010 |
| WO | WO 2013/015443 A1 | 1/2013 |

* cited by examiner (a)

(b)

(a)

(b)

(c)

(d)

(e)

(a)

(b)

(a)

(b)

SENSOR APPARATUS

CROSS-REFERENCE TO RELATED APPLICATION

This application is a 371 National Phase application of International Application No. PCT/JP2014/075065 filed on Sep. 22, 2014 which claims the benefit of Japanese Application No. 2013-247447, filed on Nov. 29, 2013, each are incorporated by reference herein in their entireties.

TECHNICAL FIELD

The present invention relates to a sensor apparatus capable of measurement on properties of an analyte liquid or constituents contained in the analyte liquid.

BACKGROUND ART

There is known a sensor apparatus which effects measurement on properties or constituents of an analyte liquid with use of a detection element such as a surface acoustic wave element (refer to Patent Literatures 1 to 3, for example).

For example, in a sensor apparatus using a surface acoustic wave element is provided with, on a piezoelectric substrate, a detection section which reacts with a constituent contained in an analyte liquid, and is configured to detect the properties or constituents of the analyte liquid by measuring variation in surface acoustic waves propagating through the detection section. Such a measurement method using the surface acoustic wave element or the like has the advantage over other measurement methods (for example, enzymatic method) in that it allows easy simultaneous detection for a plurality of characteristics to be inspected.

However, each conventional sensor apparatus using a detection element such as the surface acoustic wave element has no mechanism capable of liquid suction built therein. Thus, in order to enable an analyte liquid to flow into the detection section, the following procedural steps are required: suction of the analyte liquid using an instrument such as a micro pipette; and delivery of the sucked analyte liquid into the detection section. This leads to an increase in the complexity of measurement operation. Furthermore, the necessity of preparation of extra instruments leads to scale-up of the measurement apparatus as a whole.

There is also known a sensor apparatus which adopts a detection method which differs from the detection method using a detection element such as the surface acoustic wave element. In this construction, a reagent containing, for example, an enzyme is applied in advance to a measuring electrode, and, a target contained in an analyte liquid is caused to react with the reagent-bearing part for the reading of electric current variation in the measuring electrode (refer to Patent Literature 4).

In Patent Literature 4, there is disclosed a technology that enables the sensor apparatus to effect suction of an analyte liquid on its own by using capillarity. According to this technology, an elongate pathway for the supply of an analyte liquid is led out to the reagent-bearing part of the measuring electrode to suck an analyte liquid so that it can be directed to the reagent-bearing part under capillarity.

Inconveniently, the analyte liquid measurement method as disclosed in Patent Literature 4 that involves application of a reagent containing an enzyme or the like to the measuring electrode does not lend itself to inspection for a plurality of characteristics because of limitations upon the number of measurable characteristics to be inspected.

In the sensor apparatus disclosed in Patent Literature 4, its measuring section is implemented by applying a reagent to an electrode, wherefore the thickness of the measuring section is equivalent to the thickness of the electrode, that is; the measuring section is very thin. This makes it possible to place the elongate pathway for the supply of analyte liquid so as to reach the measuring section without discontinuity.

On the other hand, in the sensor apparatus using a detection element such as the surface acoustic wave element, the detection element is formed of a piezoelectric substrate or the like, and thus has a certain thickness. In this case, even if the technology disclosed in Patent Literature 4 is applied, the pathway for analyte liquid supply may be obstructed by the detection element, thus making it difficult to cause an analyte liquid to flow into the detection section.

CITATION LIST

Patent Literature

Patent Literature 1: Japanese Unexamined Patent Publication JP-A 5-240762 (1993)
Patent Literature 2: Japanese Unexamined Patent Publication JP-A 2006-184011
Patent Literature 3: Japanese Unexamined Patent Publication JP-A 2010-239477
Patent Literature 4: Japanese Unexamined Patent Publication JP-A 2005-249491

SUMMARY OF INVENTION

Technical Problem

There has thus been sought after a sensor apparatus which employs a detection element such as a surface acoustic wave element having a certain thickness for its detection section and yet includes a suction mechanism capable of feeding an analyte liquid to the detection section properly.

Solution to Problem

According to an embodiment of the invention, a sensor includes: an inflow section into which an analyte liquid flows; a first cover member; a detection element comprising an element substrate located on an upper surface of the first cover member, and a detection section which is located on an upper surface of the element substrate and is configured to detect a target contained in an analyte liquid; an intermediate cover member comprising a first upstream portion which is located on the upper surface of the first cover member and is located on a side of the inflow section with respect to the detection element; a second cover member which covers the detection element, joins to at least one of the first cover member and the intermediate cover member, and comprises a second upstream portion located on a side of the inflow section with respect to the detection element; and a flow channel which is surrounded by the intermediate cover member and the second cover member, is continuous with the inflow section, and extends at least to the detection section, wherein a contact angle $\theta 2a$ of a lower surface of the second upstream portion of the second cover member with the analyte liquid is smaller than a contact angle $\theta 3$ of the upper surface of the detection element with the analyte liquid.

Moreover, according to another embodiment of the invention, a sensor apparatus includes: an inflow section into which an analyte liquid flows; a first cover member; a detection element comprising an element substrate located on an upper surface of the first cover member, and a detection section which is located on an upper surface of the element substrate and is configured to detect a target contained in an analyte liquid; an intermediate cover member comprising a first upstream portion which is located on the upper surface of the first cover member and is located on a side of the inflow section with respect to the detection element; a second cover member which covers the detection element, joins to at least one of the first cover member and the intermediate cover member, and comprises a second upstream portion located on a side of the inflow section with respect to the detection element; and a flow channel which is surrounded by the intermediate cover member and the second cover member, is continuous with the inflow section, and extends at least to the detection section, wherein a contact angle θ1a of the upper surface of the first upstream portion of the intermediate cover member with the analyte liquid is smaller than a contact angle θ3 of the upper surface of the detection element with the analyte liquid.

According to such a sensor apparatus, the detection element and the intermediate cover member which constitutes at least part of the flow channel are juxtaposed on the upper surface of the first cover member. Thus, even with use of the detection element having a certain thickness, an analyte liquid flow channel extending from the inflow section to the detection section can be provided, wherefore the analyte liquid sucked through the inflow section under capillarity, for example, can be delivered to the detection section efficiently. That is, the sensor apparatus uses the detection element having a certain thickness and yet includes an analyte liquid suction mechanism built in itself, and is thus capable of measurement operation in a simple way. Moreover, in the analyte liquid flow channel, the contact angle θ1a, θ2a of the surface of the member located upstream of the detection element with the analyte liquid is smaller than the contact angle θ3 of the surface of the detection element with the analyte liquid, thus enabling the analyte liquid which has flowed into the flow channel from the inflow section to flow smoothly over the surface of the member located on the upstream side and eventually reach the detection element (detection section) effectively.

BRIEF DESCRIPTION OF DRAWINGS

FIG. 1(a) is a plan view, FIG. 1(b) is a lengthwise sectional view, and FIG. 1(c) is a widthwise sectional view;

FIG. 8(a) is a plan view, FIG. 8(b) is a lengthwise sectional view, and FIG. 8(c) is a widthwise sectional view;

FIG. 13(a) is a plan view and FIG. 13(b) is a lengthwise sectional view;

FIG. 14(a) is a plan view and FIG. 14(b) is a lengthwise sectional view.

DESCRIPTION OF EMBODIMENTS

Hereinafter, embodiments of a sensor apparatus according to the invention will be described in detail with reference to drawings. In each drawing to be referred to in the following description, like constituent members are identified with the same reference symbols. Moreover, for example, the size of each member and the distance between the individual members are schematically shown in each drawing and may therefore be different from the actual measurements.

First Embodiment

A sensor apparatus 100 in accordance with a first embodiment of the invention will be described with reference to FIGS. 1 to 5.

Figure 1:
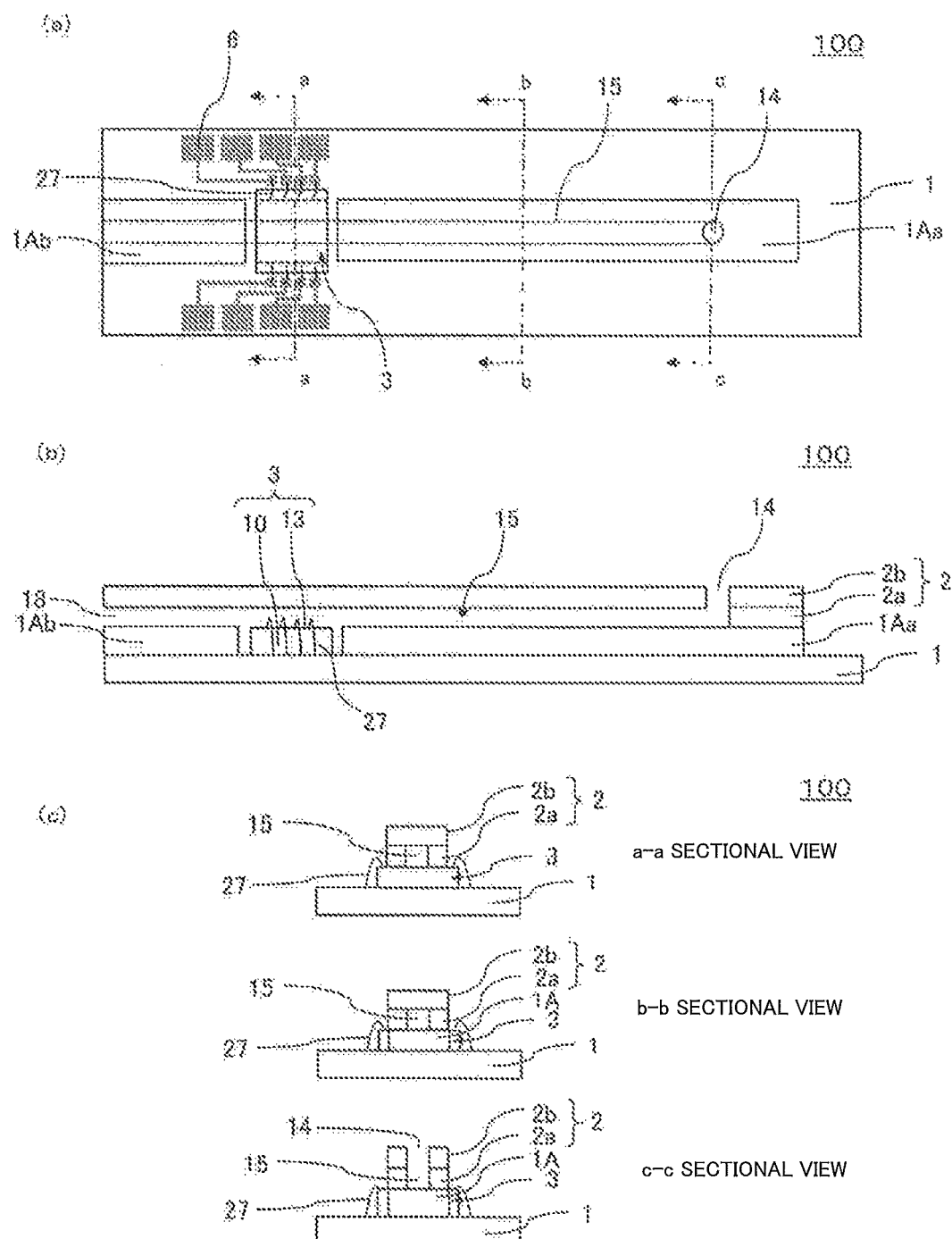
FIG. 1 is a view showing a sensor apparatus in accordance with a first embodiment of the invention.

As shown in FIG. 1, the sensor apparatus 100 of this embodiment mainly comprises: a first cover member 1; an intermediate cover member 1A; a second cover member 2; and a detection element 3.

Specifically, as shown in FIG. 1(b), the sensor apparatus 100 includes an inflow section 14 into which an analyte liquid flows, and a flow channel 15 which is continuous with the inflow section 14, is surrounded by the intermediate cover member 1A and the second cover member 2, and extends at least to a detection section 13. In FIG. 1(c) which is a sectional view corresponding to FIG. 1(a), there are shown, in top-to-bottom order, an a-a section, a b-b section, and a c-c section. As shown in FIG. 1(b), the inflow section 14 is located at side surfaces of the intermediate cover member 1A and the second cover member 2. The inflow section 14 may be configured to pass through the second cover member 2 in a thickness direction thereof as shown in FIG. 1(b). It is possible to impart hydrophobicity to an inner wall near the inflow section 14, or an outer surface near the inflow section 14, as contrasted to the nearby flow channel 15. This enables an analyte liquid dwelling around the inflow section 14 to flow into the flow channel 15 readily.

In the sensor apparatus 100 of this embodiment, the detection element and the intermediate cover member which constitutes at least part of the flow channel are juxtaposed on the upper surface of the first cover member. In this case, even with use of the detection element having a certain thickness, an analyte liquid flow channel extending from the inflow section to the detection section can be ensured, wherefore the analyte liquid sucked through the inflow section under capillarity, for example, can be delivered to the detection section properly. That is, there can be provided the sensor apparatus which uses the detection element having a certain thickness and yet includes an analyte liquid suction mechanism built in itself, and is thus capable of measurement operation in a simple way. Moreover, in the analyte liquid flow channel, a contact angle θ1a, θ2a, which is an angle of contact of a surface of a member located upstream of the detection element with the analyte liquid, is smaller than a contact angle θ3 which is an angle of contact of the surface of the detection element with the analyte liquid, thus enabling the analyte liquid which has flowed into the flow channel from the inflow section to flow smoothly to the detection element (detection section) over the surface of the member located on the upstream side.

(First Cover Member 1)

As shown in FIG. 1(b), the first cover member 1 is shaped like a flat plate. Its thickness falls in the range of 0.1 mm to 1.5 mm, for example. The first cover member 1 has substantially a rectangular planar configuration. The longitudinal length of the first cover member 1 falls in the range of 1 cm to 8 cm, for example, and, the widthwise length thereof falls in the range of 1 cm to 3 cm, for example. For example, paper, plastics, celluloid, ceramics, non-woven fabric, or glass may be used as the material of the first cover member 1. The use of plastics is desirable from the standpoint of required strength and cost.

Moreover, as shown in FIG. 1(a), on the upper surface of the first cover member 1 are formed a terminal 6 and a wiring line 7 routed from the terminal 6 to a position near the detection element 3. The terminal 6 is formed on the upper surface of the intermediate cover member 1A so as to lie on each side of the detection element 3 in a widthwise direction. When the sensor apparatus 100 is subjected to measurement using an external measuring apparatus (not shown in the drawing), the terminal 6 and the external measuring apparatus are electrically connected to each other. Moreover, the terminal 6 and the detection element 3 are electrically connected to each other via, for example, the wiring line 7. A signal sent from the external measuring apparatus is inputted to the sensor apparatus 100 via the terminal 6, and, a signal sent from the sensor apparatus 100 is outputted to the external measuring apparatus via the terminal 6.

(Intermediate Cover Member 1A)

In this embodiment, as shown in FIG. 1(a), the intermediate cover member 1A is placed side by side with the detection element 3 on the upper surface of the first cover member 1. Moreover, the intermediate cover member 1A and the detection element 3 are located with a gap.

The intermediate cover member 1A has the form of a flat frame constructed of a flat plate having a recess-forming area 4, and, its thickness falls in the range of 0.1 mm to 0.5 mm, for example.

In this embodiment, as shown in FIG. 1(a), the recess-forming area 4 acts as a partition between a first upstream portion 1Aa and a first downstream portion 1Ab. The intermediate cover member 1A provided with the recess-forming area 4 is joined to the flat plate-shaped first cover member 1, whereupon an element receiving recess 5 is defined by the joining together of the first cover member 1 and the intermediate cover member 1A. That is, the upper surface of the first cover member 1 located inside the recess-forming area 4 becomes the bottom surface of the element receiving recess 5, and the inner wall of the recess-forming area 4 becomes the inner wall of the element receiving recess 5.

As the material of the intermediate cover member 1A, use can be made of, for example, resin (including plastics), paper, non-woven fabric, and glass, and, more specifically, resin materials such as polyester resin, polyethylene resin, acrylic resin, and silicone resin are desirable for use. The first cover member 1 and the intermediate cover member 1A may be made of different materials.

Moreover, in this embodiment, the intermediate cover member 1A comprises the first upstream portion 1Aa and the first downstream portion 1Ab. As shown in FIG. 1(a), when viewed from above, the detection element 3 is located between the first upstream portion 1Aa and the first downstream portion 1Ab. In this case, when an analyte liquid flows out over the detection element 3 after passing through part of the flow channel 15 corresponding to the first upstream portion 1Aa, an excess of the analyte liquid over an amount required for measurement flows toward the first downstream portion 1Ab, wherefore an adequate amount of the analyte liquid can be fed to the detection element 3.

It is preferable that the intermediate cover member 1A is larger in thickness than the detection element 3.

(Second Cover Member 2)

As shown in FIG. 1(b), the second cover member 2 covers at least part of the detection element 3, and is joined to the intermediate cover member 1A. As the material of the second cover member 2, use can be made of, for example, resin (including plastics), paper, non-woven fabric, and glass, and, more specifically, resin materials such as polyester resin, polyethylene resin, acrylic resin, and silicone resin are desirable for use. The first cover member 1 and the second cover member 2 may be made of the same material. In this case, deformation resulting from the difference in thermal expansion coefficient between the first and second cover members can be minimized. The second cover member 2 may be joined only to the intermediate cover member 1A, or be joined to both of the first cover member 1 and the intermediate cover member 1A.

The second cover member 2 comprises a third substrate 2a and a fourth substrate 2b.

The third substrate 2a is bonded to the upper surface of the intermediate cover member 1A. The third substrate 2a is shaped like a flat plate having a thickness of 0.1 mm to 0.5 mm, for example. The fourth substrate 2b is bonded to the upper surface of the third substrate 2a. The fourth substrate 2b is shaped like a flat plate having a thickness of 0.1 mm to 0.5 mm, for example. By joining the fourth substrate 2b to the third substrate 2a, as shown in FIG. 1(b), the flow channel 15 is formed on the lower surface of the second cover member 2. The flow channel 15 extends from the inflow section 14 to at least a region immediately above the detection section 13, and has a rectangular sectional profile, for example. The third substrate 2a and the fourth substrate 2b may be made of the same material, or an unitary construction of the combined third and fourth substrates 2a and 2b may be used.

In this embodiment, as shown in FIG. 1(b), at an end of the flow channel 15, the third substrate 2a is not placed, and a gap between the fourth substrate 2b and the intermediate cover member 1A serves as an exhaust hole 18. The exhaust hole 18 is provided to let air, for example, in the flow channel 15 go out. The opening of the exhaust hole 18 may be given any shape which is capable of release of air in the flow channel 15, for example, a circular shape or a quadrangular shape. Note that formation of the exhaust hole 18 having a too large opening leads to an increase in the area of part of an analyte liquid present in the flow channel 15 which part is exposed to outside air, thus causing an evaporation of a water content in the analyte liquid. In consequence, the analyte liquid is prone to changes in concentration, which will result in poor measurement accuracy. It is therefore preferable that the exhaust hole 18 is configured so as not to have an unnecessarily large opening. Specifically, in the case of forming a circular exhaust hole 18, its diameter is less than or equal to 2 mm, and, in the case of forming a quadrangular exhaust hole 18, each side thereof has a length of less than or equal to 2 mm. It is also possible to impart hydrophobicity to an inner wall near the exhaust hole 18, or an outer surface near the exhaust hole 18, as contrasted to the nearby flow channel 15. This helps restrain an analyte liquid filled in the flow channel 15 from leaking to the outside through the exhaust hole 18.

All of the first cover member 1, the intermediate cover member 1A, and the second cover member 2 may be made of the same material. In this case, these members may be rendered substantially uniform in thermal expansion coefficient, thus minimizing deformation resulting from the difference in thermal expansion coefficient among the members. Moreover, there may be a case where a biomaterial is applied to the detection section 13, and, external light, such as ultraviolet rays, will alter the quality of some biomaterials. In this regard, it is advisable to use an opaque material having light-blocking capability as the materials of the first cover member 1, the intermediate cover member 1A, and the second cover member 2. On the other hand, in a case where external light-induced quality degradation will hardly occur in the detection section 13, the second cover member 2 constituting the flow channel 15 may be made of a nearly transparent material. In this case, the condition of an analyte liquid flowing through the interior of the flow channel 15 can be visually checked, thus permitting the combined use of an optical detection system.

(Detection Element 3)

Figure 2:
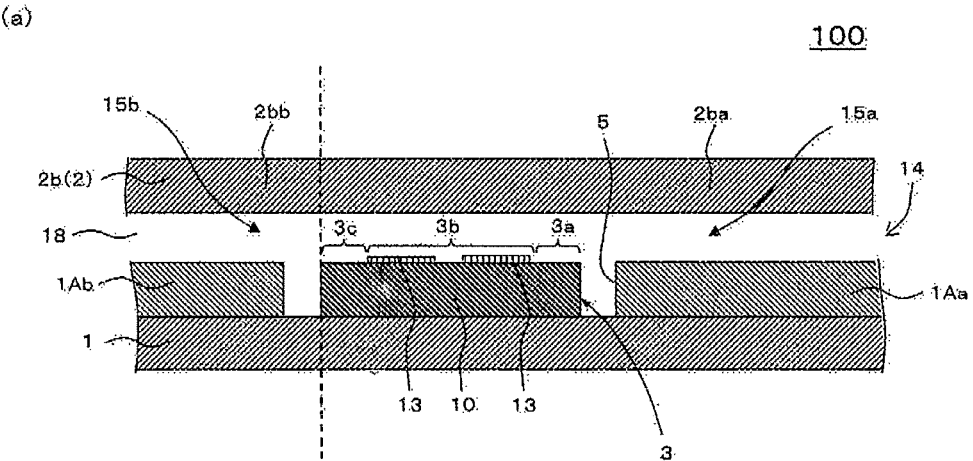
FIG. 2 is an enlarged sectional view showing part of the sensor apparatus shown in FIG. 1.
Figure 2:
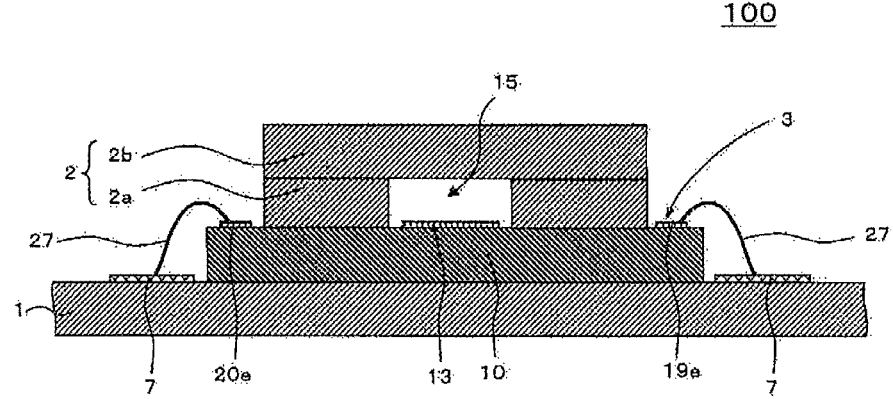

As shown in FIG. 1(*b*), the detection element 3 comprises: an element substrate 10 located on the upper surface of the first cover member 1; and at least one detection section 13 which is located on the upper surface of the element substrate 10 and is configured to detect a target contained in an analyte liquid. The details of the detection element 3 are shown in FIG. 2(*b*) and FIG. 3.

Figure 3:
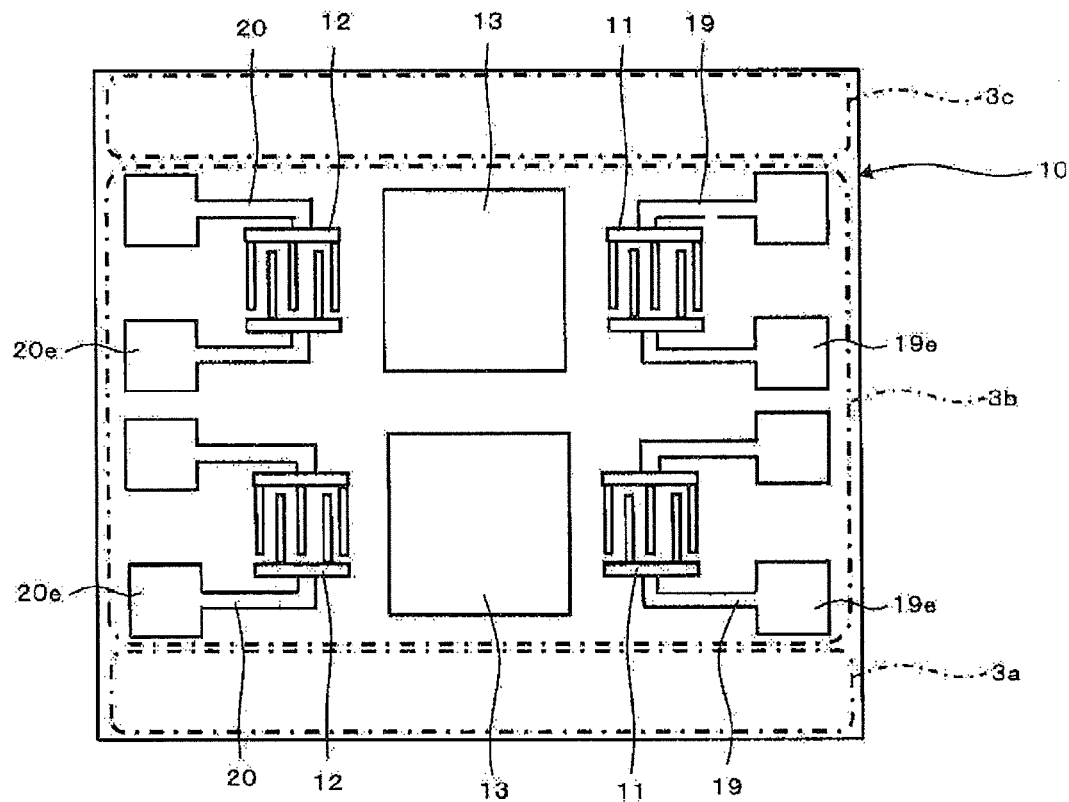
FIG. 3 is a plan view showing a detection element of the sensor apparatus shown in FIG. 1.
Figure 4:
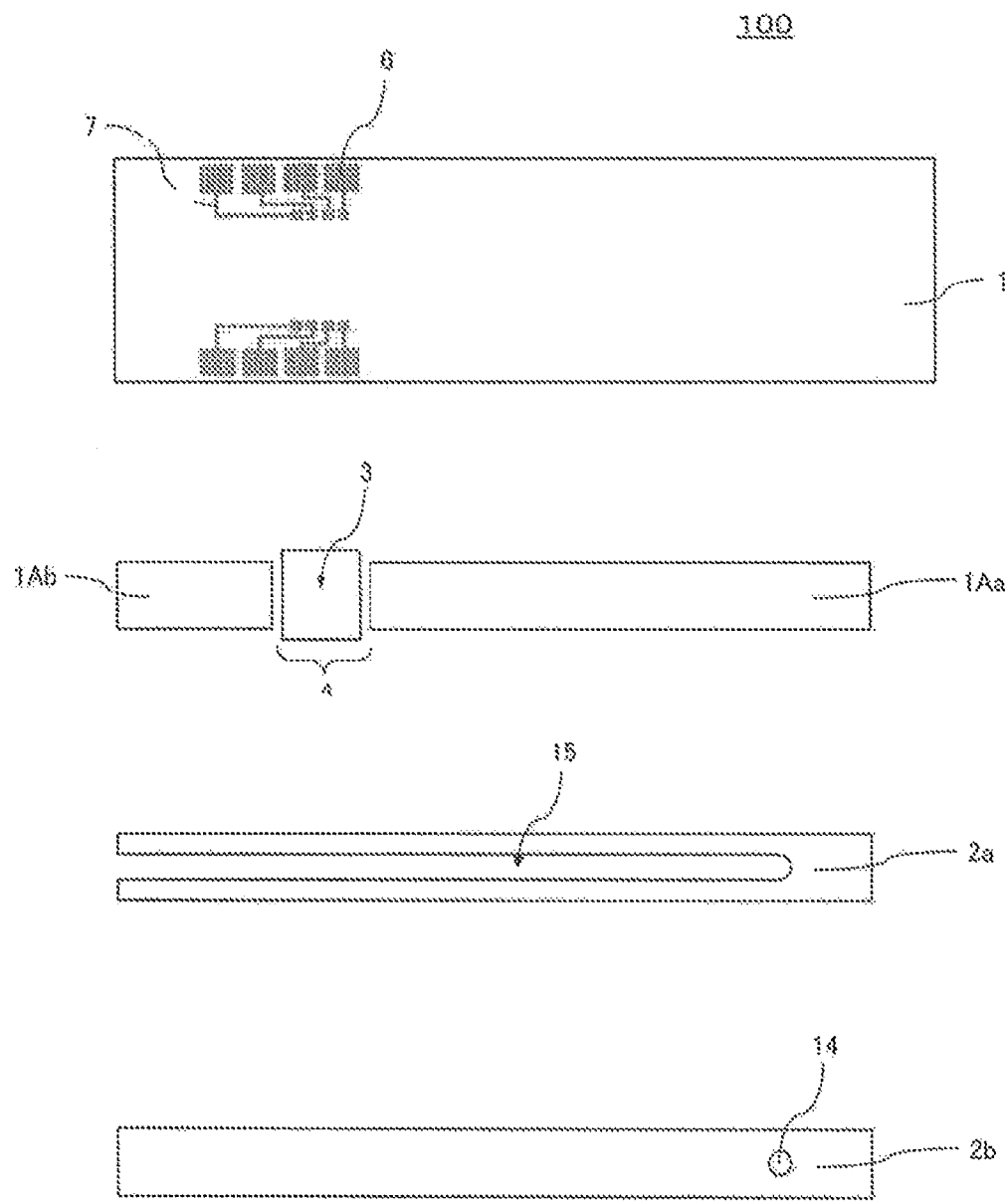
FIG. 4 is an exploded plan view of the sensor apparatus shown in FIG. 1.

In this embodiment, as shown in FIG. 3, an electrode pattern is provided on the upper surface of the element substrate 10, and, on an as needed basis, an insulating member 28 may be provided so as to cover the electrode pattern. When an SAW element is used as the detection element 3, the electrode pattern corresponds to an IDT (InterDigital Transducer) electrode. In this embodiment, on the upper surface of the element substrate 10 are disposed a first IDT electrode 11, a second IDT electrode 12, a first extraction electrode 19, a second extraction electrode 20, and so forth that will hereafter be described. In this embodiment, as shown in FIG. 2(*b*), on the upper surface of the element substrate 10, the second cover member 2 is fixed above the IDT electrodes 11 and 12, for example.

(Element Substrate 10)

The element substrate 10 is constructed of a substrate of single crystal having piezoelectric properties such for example as lithium tantalate ($LiTaO_3$) single crystal, lithium niobate ($LiNbO_3$) single crystal, or quartz. The planar configuration and dimensions of the element substrate 10 are determined properly. By way of example, the element substrate 10 has a thickness of 0.3 mm to 1 mm.

(IDT Electrode 11, 12)

As shown in FIG. 3, the first IDT electrode 11 comprises a pair of comb-like electrodes. The pair of comb-like electrode includes two bus bars opposed to each other and a plurality of electrode fingers which extend from one of the bus bars toward the other bus bar, and from the other bus bar to the one bus bar. The pair of comb-like electrodes is placed so that the plurality of electrode fingers are disposed in an interdigital manner. The second IDT electrode 12 is similar in configuration to the first IDT electrode 11. The first IDT electrode 11 and the second IDT electrode 12 constitute a transversal IDT electrode.

The first IDT electrode 11 is configured to generate a predetermined surface acoustic wave (SAW), and the second IDT electrode 12 is configured to receive the SAW generated in the first IDT electrode 11. The first IDT electrode 11 and the second IDT electrode 12 are located on the same straight line so as to allow the second IDT electrode 12 to receive the SAW generated in the first IDT electrode 11. The design of frequency response characteristics is based on the number of the electrode fingers of the first IDT electrode 11 and the second IDT electrode 12, the distance between the adjacent electrode fingers, the crossing width of the electrode fingers, etc., serving as parameters. While SAWs of various vibration modes are excited by IDT electrodes, for example, the vibration mode of a transversal wave called an SH wave is utilized in the detection element 3 of the present embodiment.

An elastic member may be disposed on an outside of the first IDT electrode 11 and the second IDT electrode 12 in the direction of SAW propagation (widthwise direction) to reduce SAW reflection. The frequency of SAW may be set within the range of several megahertz (MHz) to several gigahertz (GHz), for example. It is advisable to set the SAW frequency within the range of several hundred MHz to 2 GHz as a matter of practicality, and, in this case, downsizing of the detection element 3 can be achieved, thus making the sensor apparatus 100 compact.

(Extraction Electrode 19, 20)

As shown in FIG. 3, the first extraction electrode 19 is connected to the first IDT electrode 11, and the second extraction electrode 20 is connected to the second IDT electrode 12. The first extraction electrode 19 is drawn from the first IDT electrode 11 in the opposite direction to the detection section 13, and, an end 19*e* of the first extraction electrode 19 is electrically connected to the wiring line 7 disposed in the first cover member 1. The second extraction electrode 20 is drawn from the second IDT electrode 12 in the opposite direction to the detection section 13, and, an end 20*e* of the second extraction electrode 20 is electrically connected to the wiring line 7.

The first IDT electrode 11, the second IDT electrode 12, the first extraction electrode 19, and the second extraction electrode 20 are made of, for example, aluminum or an alloy of aluminum and copper. Moreover, these electrodes may be designed to have a multilayer structure. In the case of adopting a multilayer structure, for example, the first layer may be composed of titanium or chromium, and the second layer may be composed of aluminum or an aluminum alloy.

(Detection Section 13)

As shown in FIG. 3, the detection section 13 is disposed between the first IDT electrode 11 and the second IDT electrode 12. For example, the detection section 13 is composed of a metal film and a nucleic acid- or peptide-made aptamer immobilized on the surface of the metal film. For example, the metal film may be given a two-layer form consisting of a chromium layer and a gold layer formed on the chromium layer. The detection section 13 undergoes reaction with a target contained in an analyte liquid, and, more specifically, upon contact of an analyte liquid with the detection section 13, a specific target contained in the analyte liquid is bound to the corresponding aptamer.

Given that the first IDT electrode, the second IDT electrode, and the detection section 13 disposed in a widthwise direction are grouped into a set, then the sensor apparatus 100 of the present embodiment is provided with two sets as shown in FIG. 3. By designing the detection section 13 of one of the sets to react with a target which differs from a target with which the detection section 13 of the other one of the sets reacts, it is possible to detect two different targets by a single sensor apparatus.

(Target Detection Using Detection Element 3)

To effect analyte liquid detection with the detection element 3 that utilizes an SAW, at first, a predetermined voltage from an external measuring apparatus is applied to the first IDT electrode 11 via the wiring line 7 and the first extraction electrode 19, for example. Then, the surface of the element substrate 10 is excited within the first IDT electrode 11-bearing region, thus producing SAW having a predetermined frequency. Part of the SAW so produced propagates toward the detection section 13, passes through the detection section 13, and reaches the second IDT electrode 12. In the detection section 13, the aptamer of the detection section 13 is bound to a specific target contained in an analyte liquid, and the weight of the detection section 13 changes correspondingly, with consequent variations in the characteristics, such as the phase, of the SAW passing under the detection section 13. In response to the arrival of the SAW which has undergone such characteristic variations at the second IDT electrode, a corresponding voltage is developed in the second IDT electrode. An output of this voltage is produced through the second extraction electrode 20, the wiring line 70, and so forth, and, by checking a readout on the outputted voltage provided by the external measuring apparatus, it is possible to determine the properties and constituents of the analyte liquid.

In the sensor apparatus 100, capillarity is utilized to direct an analyte liquid to the detection section 13.

Specifically, as described earlier, by joining the second cover member 2 to the intermediate cover member 1A, the flow channel 15 is created in the form of an elongate pipe on the lower surface of the second cover member 2. Thus, for example, by setting the width or the diameter of the flow channel 15 at a predetermined value with consideration given to, for example, the type of an analyte liquid and the constituent materials of the intermediate cover member 1A and the second cover member 2, it is possible to cause capillarity in the flow channel 15 in the form of an elongate pipe. The width of the flow channel 15 falls in the range of 0.5 mm to 3 mm, for example, and, the depth thereof falls in the range of 0.1 mm to 0.5 mm, for example. The flow channel 15 has a downstream part (extension) 15b which is a part extending beyond the detection section 13, and, the second cover member 2 is provided with the exhaust hole 18 which is continuous with the extension 15b. When an analyte liquid enters the flow channel 15, air present in the flow channel 15 is expelled out of the exhaust hole 18.

In the case where such a pipe causing capillarity is defined by the cover member including the intermediate cover member 1A and the second cover member 2, upon contact with the inflow section 14, an analyte liquid is sucked into the interior of the cover member while passing through the flow channel 15. Thus, the sensor apparatus 100 has an analyte liquid suction mechanism built in itself, and is therefore capable of suction of an analyte liquid without using an instrument such as a pipette.

(Lyophilicity of Flow Channel 15)

In the sensor apparatus 100 of this embodiment, the whole or part of the inner surface of the flow channel 15, for example, the bottom surface and the wall surface of the flow channel 15 have lyophilicity. In the flow channel 15 having such a lyophilic inner surface, capillarity can be caused readily, thus facilitating suction of an analyte liquid from the inflow section 14.

A lyophilic part of the inner surface of the flow channel 15 is designed to have an angle of contact with water of less than or equal to 60°. Capillarity is caused more readily when the contact angle is less than or equal to 60°, and thus, upon contact with the inflow section, an analyte liquid can be sucked into the flow channel 15 more reliably. Now, a detailed description will be given below with reference to FIG. 2(a). FIG. 2(a) is an enlarged sectional view showing part of the sensor apparatus 100 shown in FIG. 1(b).

In this embodiment, the contact angle $\theta 2a$ of the lower surface of a second upstream portion 2a of the second cover member 2 with an analyte liquid, or the contact angle $\theta 1a$ of the upper surface of the first upstream portion 1Aa of the intermediate cover member 1A with an analyte liquid, is smaller than the contact angle $\theta 3$ of the upper surface of the detection element 3 with an analyte liquid. In this case, in the analyte liquid flow channel, the contact angle $\theta 1a$, $\theta 2a$ of the surface of the member located upstream of the detection element with an analyte liquid is smaller than the contact angle $\theta 3$ of the surface of the detection element with an analyte liquid, thus enabling an analyte liquid which has flowed into the flow channel from the inflow section under capillarity to flow smoothly over the surface of the member located on the upstream side and eventually reach the detection element (detection section) effectively.

Moreover, the contact angle $\theta 2a$ of the lower surface of the second upstream portion 2a of the second cover member 2 with an analyte liquid is advisably set to be equal to or smaller than the contact angle $\theta 1a$ of the upper surface of the first upstream portion 1Aa of the intermediate cover member 1A with an analyte liquid. In this case, an analyte liquid can be guided efficiently toward the detection element 13 by the lower surface of the second upstream portion 2a of the second cover member 2 and the upper surface of the first upstream portion 1Aa of the intermediate cover member 1A which define the flow channel 15. By setting the contact angle $\theta 2a$ to be smaller than the contact angle $\theta 1a$, even if a gap is left between the upper surface of the first upstream portion 1Aa constituting the intermediate cover member 1A and the detection element 13, it is possible to cause an analyte liquid to run over the lower surface of the second upstream portion 2a of the second cover member 2 extending to the detection section 13, and thereby guide the analyte liquid toward the detection element 13 more efficiently.

Moreover, in the intermediate cover member 1A, a contact angle $\theta 1b$ of the upper surface of the first downstream portion 1Ab with an analyte liquid is advisably set to be greater than the contact angle $\theta 1a$. In this case, an analyte liquid flows through a part of the flow channel 15 located upstream of the detection element 3 (detection section 13) more smoothly than part of the flow channel 15 located downstream of the detection element 3. Moreover, in this case, after reaching the detection element 3 (detection section 13), relatively, the analyte liquid flows more slowly, wherefore a limited amount of analyte is allowed to run at a constant speed for a relatively long period of time, and thus the reaction proceeds slowly. This makes it possible to effect measurement operation with little measurement variations. It is also possible to restrain a discharge liquid which has passed over the detection element 3 (detection section 13) from leaking out of the sensor apparatus.

Moreover, in the second cover member 2, a contact angle θ2b of the upper surface of the second downstream portion 2b with an analyte liquid is advisably set to be greater than the contact angle θ2a. In this case, an analyte liquid flows through part of the flow channel 15 located upstream of the detection element 3 more smoothly than a part of the flow channel 15 located downstream of the detection element 3. Moreover, in this case, after reaching the detection element 3 (detection section 13), relatively, the analyte liquid flows more slowly, wherefore a limited amount of analyte is allowed to run at a constant speed for a relatively long period of time, and thus the reaction proceeds slowly. This makes it possible to effect measurement operation with little measurement variations. It is also possible to restrain a discharge liquid which has passed over the detection element 3 (detection section 13) from leaking out of the sensor apparatus.

Moreover, in the detection element 3, a contact angle θ3a of an upstream region 3a with an analyte liquid is advisably set to be smaller than a contact angle θ3b of a detection section 3b (13) with an analyte liquid. In this case, an analyte liquid flows smoothly through part of the flow channel 15 located upstream of the detection element 3 (detection section 13), and is therefore guided effectively toward the detection element 3 (detection section 13). Moreover, even if a gap is left between the upper surface of the first upstream portion 1Aa of the intermediate cover member 1A and the detection element 13, an analyte liquid can be guided toward the detection element 13 more efficiently by the lower surface of the second upstream portion 2a of the second cover member 2 extending to the detection section 13. Furthermore, a contact angle θ3c of a downstream region 3c with an analyte liquid is advisably set to be smaller than the contact angle θ3b of the detection section 3b (13) with an analyte liquid. In this case, a force which sets upon an analyte liquid to flow toward the downstream region 3c is exerted more strongly relative to a force acting on the analyte liquid at the detection section 3b (13), wherefore the analyte liquid which has undergone detection process in the detection section 3b (13) is restrained from still dwelling on the detection section 3b (13). Moreover, since the analyte liquid flows relatively more slowly after passing over the detection element 3 (detection section 13), it follows that the reaction proceeds slowly, thus effecting measurement operation with little measurement variations. In addition, the contact angle θ3a is advisably set to be smaller than the contact angle θ3c. In this case, the analyte liquid flows smoothly through part of the flow channel 15 corresponding to the upstream region 3a of the detection element 3 (detection section 13), and is therefore guided effectively toward the detection element 3 (detection section 13). Moreover, since the analyte liquid flows over the downstream region 3c at a slower pace after passing over the detection element 3 (detection section 13), it follows that the reaction proceeds slowly, thus effecting measurement operation with little measurement variations.

The above-mentioned contact angle θ of each member surface with an analyte liquid is measured in the following manner.

At first, a water droplet is formed by putting a drop of an analyte liquid onto the surface of an object under contact angle θ measurement. Note that water is used in place of the analyte liquid, and, the volume of the water droplet falls in the range of 1 μl to 4 μl. The measurement is effected at a room temperature of 25 to 30° C. and at a humidity of 40 to 60%.

Within 1 minute after the formation a water droplet, the water droplet is photographed in a direction toward a surface of an object, as well as in a horizontal direction, to obtain images of the shape of the water droplet.

After that, a contact angle is determined by calculation using the tangential method on the basis of the shape of the water droplet. Given that an area around an end point of the water droplet (the boundary of the substance, the water droplet, and air) is part of a sphere, the center of the sphere is determined on the basis of a plurality of points on an arc, so that the tangent to a circle at the end point of the water droplet can be derived. An angle formed by this tangent and the surface of the object is defined as the contact angle.

When the surface of the measurement target is made of a single material, the droplet-forming position is set at a region including the center of gravity of the surface on the assumption that the material has uniform mass distribution and thickness distribution. On the other hand, when the surface of the measurement target is made of a plurality of materials, the droplet-forming position is set at a region including the center of gravity of the surface on the assumption that each material has uniform mass distribution and thickness distribution. In this case, the angle of contact with the surface of the object takes on a value obtained by calculating a weighted average of the area proportions of the individual materials used as weights.

When it is desired to effect measurement operation with higher accuracy, a plurality of regions are subjected to contact angle measurement, and the mean value of all the measurement data on the individual regions is obtained.

Examples of the way to impart lyophilicity to the inner surface of the flow channel 15 include: performing lyophilic treatment on the inner surface of the flow channel 15; bonding a lyophilic film to the inner surface of the flow channel 15; and forming the cover member 2 defining the flow channel 15 from a lyophilic material. In the case of adopting the method of performing lyophilic treatment on the inner surface of the flow channel 15 or the method of bonding a lyophilic film to the inner surface of the flow channel 15 in particular, since an analyte liquid flows through the interior of the flow channel 15 while running along the lyophilic part, it is possible to restrain the analyte liquid from flowing toward an unintended area, and thereby achieve highly accurate measurement. Moreover, these methods allow occurrence of capillarity even with use of the cover member made of a lyophobic material, thus extending the range of choices of materials that can be used for the cover member.

According to the method of performing lyophilic treatment on the inner surface of the flow channel 15, for example, after the inner surface of the flow channel 15 is subjected to oxygen plasma ashing to change the functional group of the surface, a silane coupling agent is applied to the inner surface, followed by application of polyethylene glycol as the last step. As an alternative, the inner surface of the flow channel 15 may be subjected to surface treatment using a treatment agent containing phosphoryl choline.

Moreover, in the method of bonding a lyophilic film, for example, a commercially available lyophilically-treated polyester- or polyethylene-made film can be used as the lyophilic film. The lyophilic film may be formed only on the upper surface, side surface, or lower surface of the flow channel 15, or be formed on a combination of these surfaces.

(Positional Relationship Between Flow Channel 15 and Detection Element 3)

In this embodiment, while the flow channel 15 for analyte liquid has a depth of about 0.3 mm, the detection element 3 has a thickness of about 0.3 mm. That is, as shown in FIG. 1(b), the depth of the flow channel 15 and the thickness of the detection element 3 are substantially equal. Therefore, if the detection element 3 lies on the flow channel 15, the flow channel 15 will be blocked. In this regard, in the sensor apparatus 100, as shown in FIGS. 1(b) and 2, the element receiving recess 5 is defined by the first cover member 1 on which is mounted the detection element 3, and the intermediate cover member 1A joined onto the first cover member 1. The detection element 3 is placed in this element receiving recess 5 to avoid blocking of the flow channel 15 for analyte liquid. That is, the depth of the element receiving recess 5 is adjusted to be substantially equal to the thickness of the detection element 3 so that the detection element 3 can be mounted inside the element receiving recess 5, thus attaining the flow channel 15.

From the viewpoint of providing a satisfactory analyte-liquid flow channel 15, as shown in FIGS. 1(b) and 2, it is advisable to adjust the heightwise distance from the bottom surface of the element receiving recess 5 to the upper surface of the element substrate 10 to be equal to or shorter (lower) than the depth of the element receiving recess 5. For example, when the height of the element substrate 10 from the bottom surface of the element receiving recess 5 is equal to the depth of the element receiving recess 5, looking down from the inflow section 14 at the inside of the flow channel 15, the bottom surface of the flow channel 15 and the detection section 13 stand at substantially the same level.

The element receiving recess 5 may be designed to be analogous in planar configuration to the element substrate 10, and, in this case, the element receiving recess 5 is made slightly larger than the element substrate 10. More specifically, the size of the element receiving recess 5 is such that a gap which measures about 200 μm is left between the periphery of the element substrate 10 and the inner wall of the element receiving recess 5 upon placement of the element substrate 10 in the element receiving recess 5.

The detection element 3 is secured to the bottom surface of the element receiving recess 5 by, for example, a die-bonding material composed predominantly of resin such as epoxy resin, polyimide resin, or silicone resin.

The end 19e of the first extraction electrode 19 and the wiring line 7 are electrically connected to each other by a metallic thin wire 27 made of Au, for example. The connection between the end 20e of the second extraction electrode 20 and the wiring line 7 is made in a similar way. Means for connecting the wiring line 7 with the first and second extraction electrodes 19 and 20 is not limited to the metallic thin wire 27, but may be of an electrically-conductive adhesive such as an Ag paste. In the presence of a gap in a region for connection between the wiring line 7 and each of the first and second extraction electrodes 19 and 20, when the second cover member 2 is bonded to the first cover member 1, the metallic thin wire 27 is protected from damage. The first extraction electrode 19, the second extraction electrode 20, the metallic thin wire 27, and the wiring line 7 are covered with an insulating member 28. By covering the first extraction electrode 19, the second extraction electrode 20, the metallic thin wire 27, and the wiring line 7 with the insulating member 28, it is possible to retard corrosion of these electrodes and components.

As described heretofore, according to the sensor apparatus 100 of the present embodiment, by placing the detection element 3 in the element receiving recess 5 of the cover member 1, it is possible to attain the analyte liquid flow channel 15 extending from the inflow section 14 to the detection section 13, and thereby cause an analyte liquid which has been drawn into the flow channel through the inflow section under, for example, capillarity to flow to the detection section 13. That is, there is provided the sensor apparatus 100 which incorporates the detection element 3 having a certain thickness and yet includes a suction mechanism built in itself.

Next, examples of modification in the sensor apparatus 100 of the first embodiment will be described.

Modified Example

Modified Example 1

Figure 5:
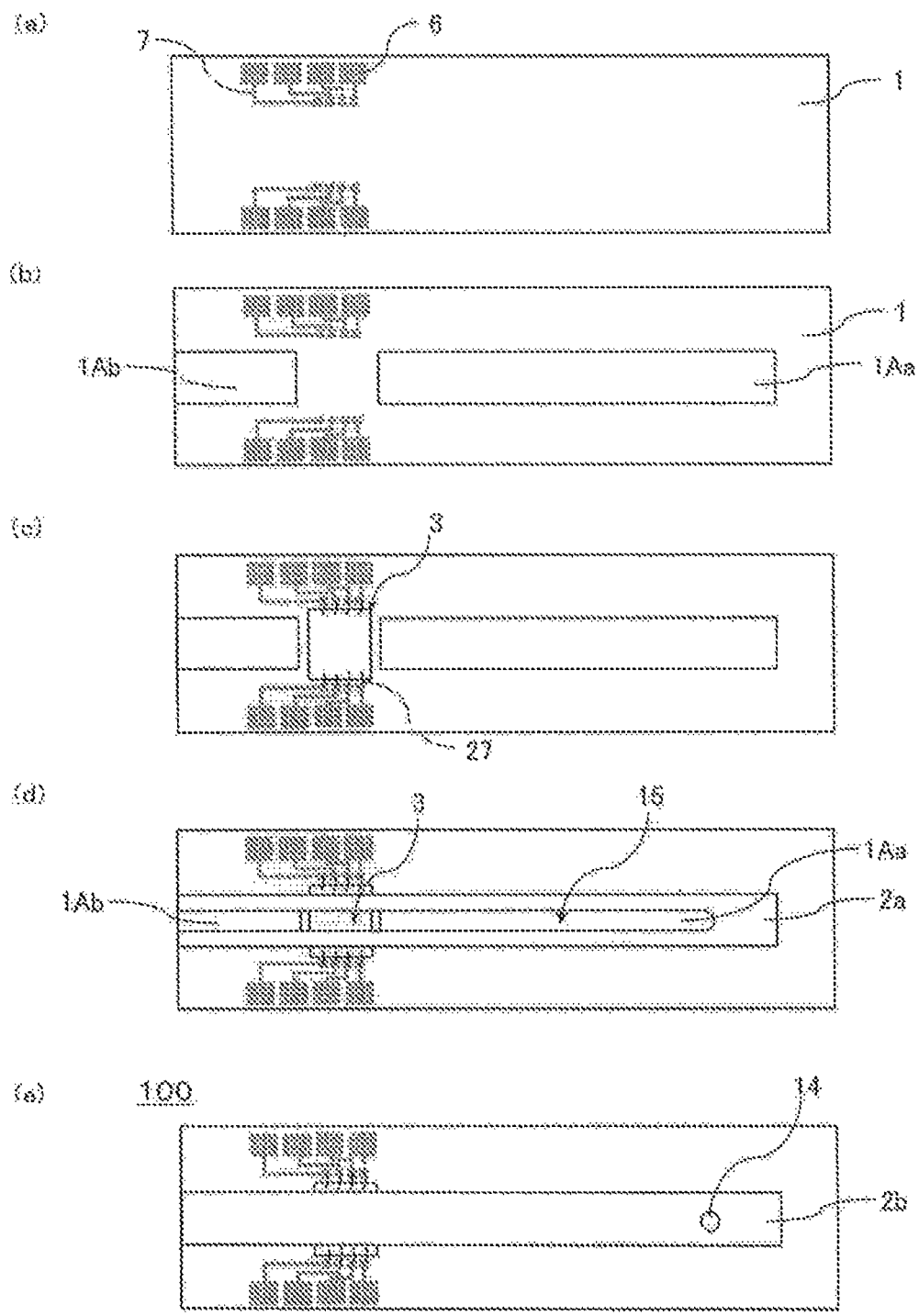
FIG. 5 is a plan view showing production steps of the sensor apparatus shown in FIG. 1.
Figure 6:
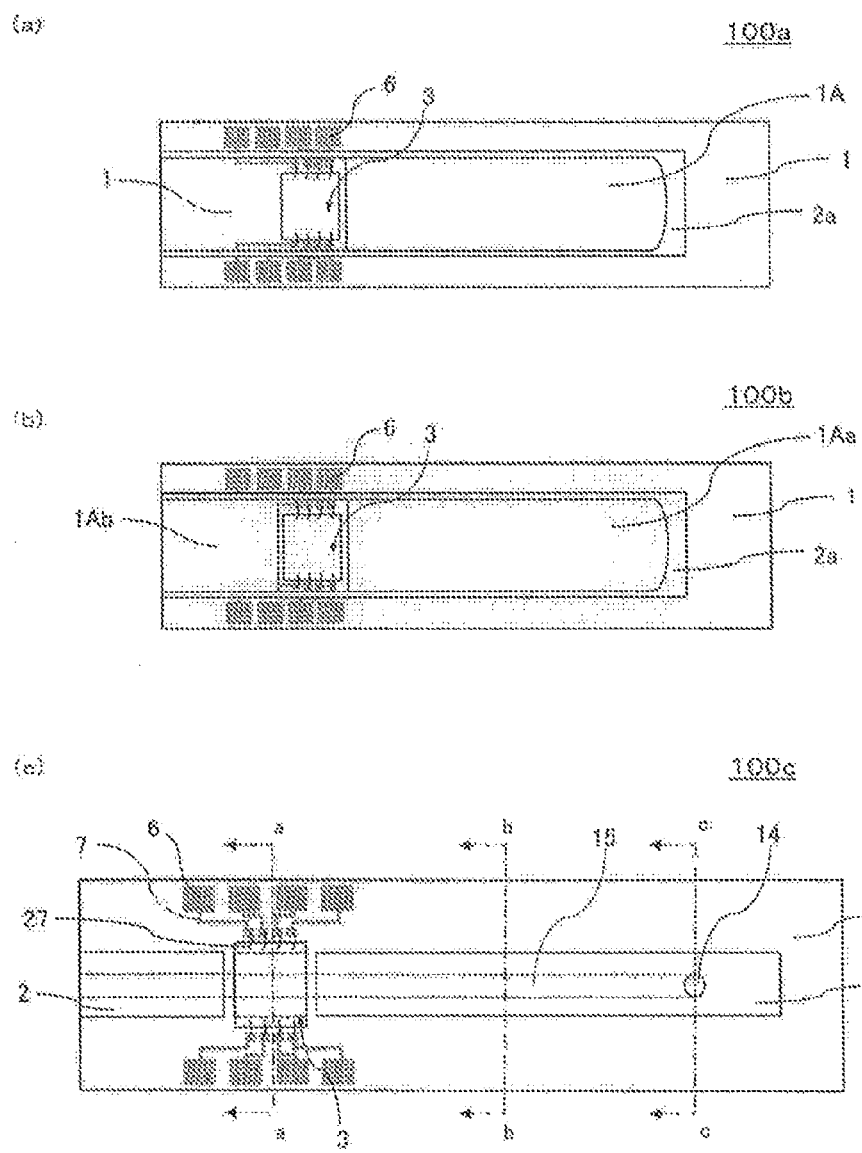
FIG. 6 is a plan view showing a modified example of the sensor apparatus shown in FIG. 1, and, FIGS. 6(a) and 6(b) correspond to FIG. 5(d), and FIG. 6(c) corresponds to FIG. 1(a)

FIG. 6 is a plan view showing sensor apparatuses 100a, 100b, and 100c which are each a modified example of the sensor apparatus 100 shown in FIG. 1, and, FIGS. 6(a) and 6(b) correspond to FIG. 5(d), and FIG. 6(c) corresponds to FIG. 1(a).

In contrast to the sensor apparatus 100 of the foregoing first embodiment, in the sensor apparatuses 100a and 100b of this modified example, the intermediate cover member 1A and the second cover member 2 are greater in width than the detection element 3. With respect to the sensor apparatus 100a, as shown in FIG. 6(a), in a region located downstream of the detection element 3, there is no intermediate cover member 1A (second downstream portion 1Ab) on the first cover member 1. On the other hand, with respect to the sensor apparatus 100b, as shown in FIG. 6(b), in the region located downstream of the detection element 3, the intermediate cover member 1A (second downstream portion 1Ab) lies on the first cover member 1.

Moreover, the sensor apparatus 100c of this modified example differs from the sensor apparatus 100 of the foregoing first embodiment in the arrangement of the terminals 6 relative to the detection element 3.

Specifically, in the sensor apparatus 100, as shown in FIG. 1, the terminals 6 are located on a side of the exhaust hole 18 with respect to the inflow section 14-side end of the detection element 3. On the other hand, in the sensor apparatus 100c of this modified example, as shown in FIG. 6(c), at least part of the terminals 6 is located on a side of the inflow section 14 with respect to the inflow section 14-side end of the detection element 3.

Moreover, in the arrangement of four terminals 6 located on one side of the detection element 3 in a longitudinal direction of the flow channel 15, the wiring lines 7 connected to two outer terminals 6, respectively, have substantially the same length, and also the wiring lines 7 connected to the other two inner terminals 6, respectively, have substantially the same length. This makes it possible to reduce variations in signals obtained by the detection element 3 depending upon the length of the wiring line 7. In this case, by establishing connections so that, when a predetermined voltage is applied from an external measurement apparatus to, for example, the first IDT electrode 11 via the wiring line 7, the first extraction electrode 19, and so forth, a potential difference occurs between one pair of the wiring lines 7 having substantially the same length set at ground potential and the other pair of the wiring lines 7 having substantially the same length, it is possible to reduce the above-mentioned signal variations, and thereby achieve an improvement in detection reliability.

Modified Example 2

Figure 7:
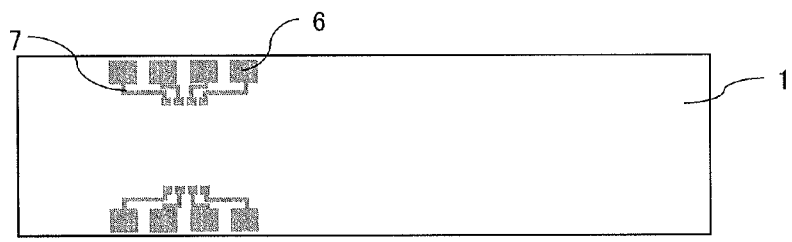
FIG. 7 is a plan view showing a modified example of the sensor apparatus shown in FIG. 1, and, FIGS. 7(a) to 7(e) each correspond to FIGS. 5(a) to 5(e)
Figure 7:
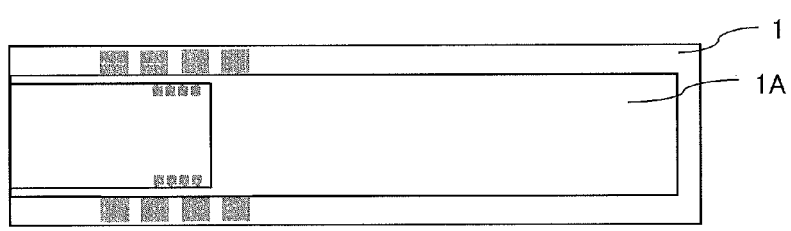
Figure 7:
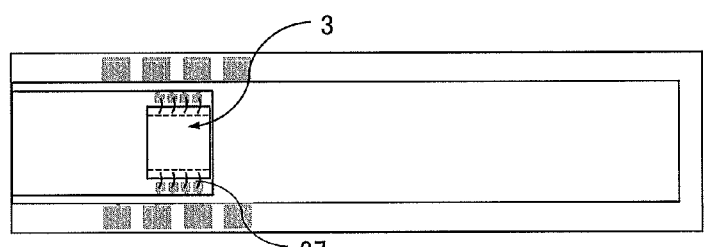
Figure 7:
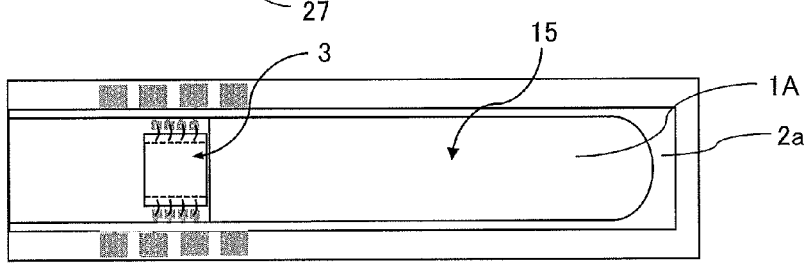
Figure 7:
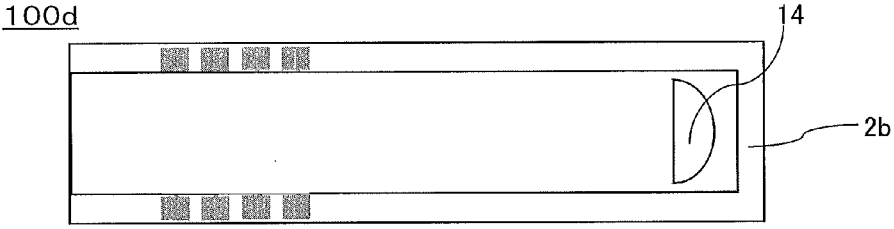

FIG. 7 is a plan view showing a sensor apparatus 100d which is a modified example of the sensor apparatus 100 shown in FIG. 1, which corresponds to FIG. 5.

The sensor apparatus 100d of this modified example, like the sensor apparatus 100c of the preceding modified example, differs from the sensor apparatus 100 of the foregoing first embodiment in the arrangement of the terminals 6 relative to the detection element 3. Thus, the sensor apparatus 100d affords the same effects as achieved by the sensor apparatus 100c of the preceding modified example.

Moreover, in contrast to the sensor apparatus 100 of the foregoing first embodiment, in the sensor apparatus 100d of this modified example, like the sensor apparatuses 100a and 100b of the preceding modified example, the intermediate cover member 1A and the second cover member 2 are greater in width than the detection element 3. This allows an analyte liquid to flow so as to cover the entire surface of the detection element 3 effectively.

Moreover, in the arrangement of four terminals 6 located on one side of the detection element 3 in the direction longitudinally of the flow channel 15, the wiring lines 7 connected to two outer terminals 6, respectively, have substantially the same length, and also the wiring lines 7 connected to the other two inner terminals 6, respectively, have substantially the same length. In this case, the difference among the four wiring lines in respect of the area of contact of an analyte liquid with the wiring line 7 left exposed at the surface of the inside of the element receiving recess 5 becomes small, thus reducing the above-mentioned signal variations.

Like the sensor apparatus 100a of the preceding modified example, as shown in FIG. 7(d), in a region located downstream of the detection element 3, there is no second downstream portion 1Ab constituting the intermediate cover member 1A on the first cover member 1. This makes it possible to suppress or reduce development of bubbles in a region located downstream of a second upstream portion 1Aa constituting the intermediate cover member 1A. In consequence, an analyte liquid can be delivered in a bubble-free state onto the detection element 3, thus achieving an improvement in sensitivity or accuracy in detection.

Modified Example 3

Figure 8:
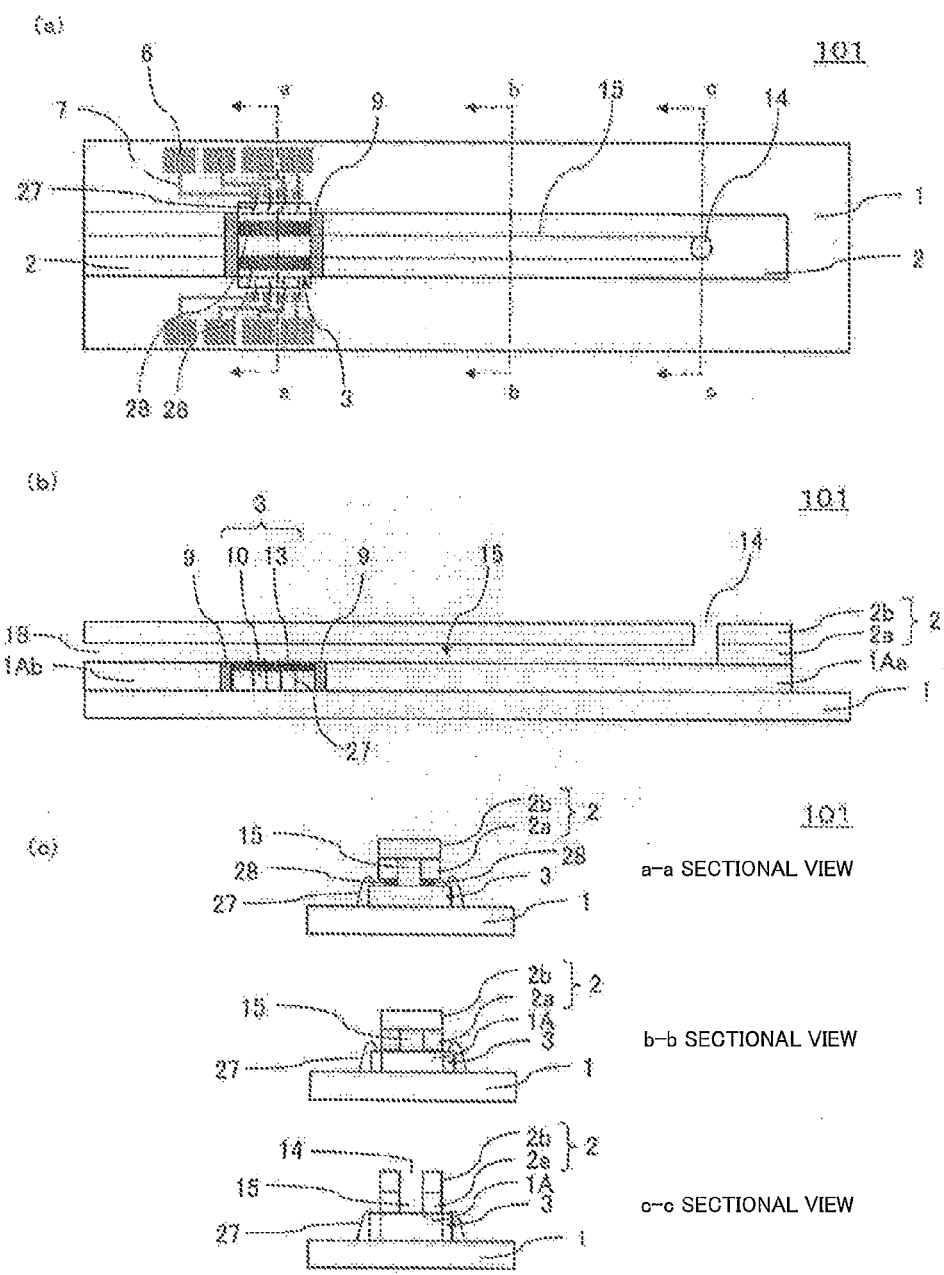
FIG. 8 is a view showing a modified example of the sensor apparatus shown in FIG. 1, and more specifically

FIG. 8 is a view showing a sensor apparatus 101 which is a modified example of the sensor apparatus 100 shown in FIG. 1, and FIG. 8(a) is a plan view, FIG. 8(b) is a lengthwise sectional view, and FIG. 8(c) is a widthwise sectional view.

In contrast to the sensor apparatus 100 of the foregoing first embodiment, in the sensor apparatus 101 of this modified example, the first IDT electrode 11 and the second IDT electrode 12 are covered with an insulating member 28.

The insulating member 28 is conducive to protection of the first IDT electrode 11 and the second IDT electrode 12 against oxidation, for example. The insulating member 28 is made of, for example, silicon oxide, aluminum oxide, zinc oxide, titanium oxide, silicon nitride, or silicon. The thickness of the insulating member 28 falls in the range of 10 nm to 2 μm, for example. The insulating member 28 is formed over the entire area of the upper surface of the element substrate 10, with the end 19e of the first extraction electrode 19 and the end 20e of the second extraction electrode 20 left uncovered.

Moreover, in contrast to the sensor apparatus 100 of the foregoing first embodiment, in the sensor apparatus 101 of this modified example, a filler member 9 is disposed in a gap between the detection element 3 and the intermediate cover member 1A.

The filler member 9 may be composed of a material which differs from the material constituting the intermediate cover member 1A and the element substrate 10, and, for example, a resin material such as PDMS can be used. The filler member 9 does not necessarily have to be provided so as to completely fill the gap between the detection element 3 and the intermediate cover member 1A, and may thus be disposed only in a part of the gap corresponding to the flow channel 15, for example. The placement of the filler member 9 in the gap between the detection element 3 and the intermediate cover member 1A makes it possible to avoid that capillarity is obstructed by the gap, and thereby achieve sucking of an analyte liquid for smooth delivery to the detection element 3.

Figure 9:
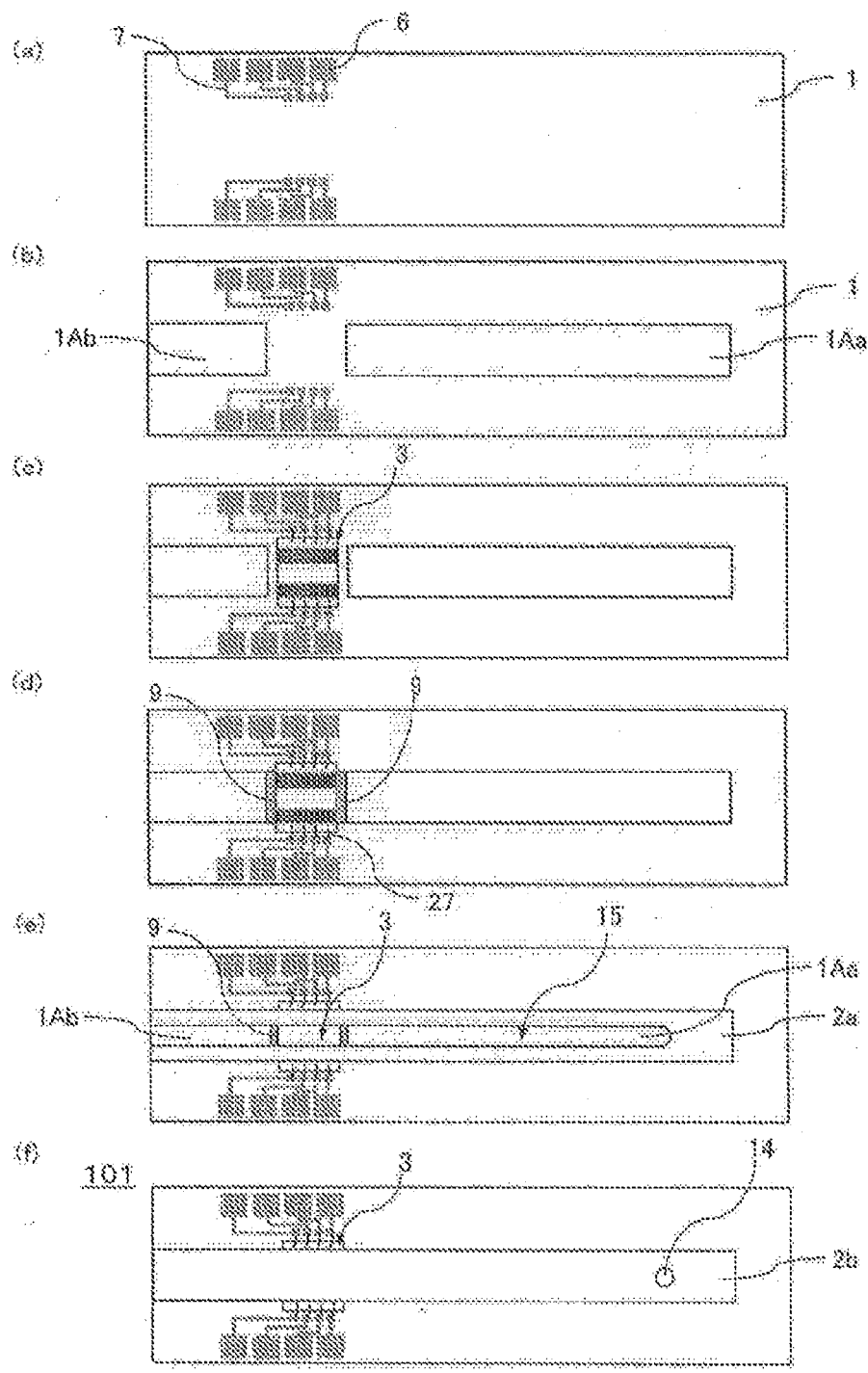
FIG. 9 is a plan view showing manufacturing steps of the sensor apparatus shown in FIG. 8.

FIG. 9 is a plan view showing manufacturing steps of the sensor apparatus 101 shown in FIG. 8.

To begin with, as shown in FIG. 9(a), the first cover member 1 provided with the terminals 6 and the wiring lines 7 is prepared.

Next, as shown in FIG. 9(b), the intermediate cover member 1A is laminated onto the first cover member 1. The intermediate cover member 1A is composed of the first upstream portion 1Aa and the first downstream portion 1Ab.

Next, as shown in FIG. 9(c), the detection element 3 is mounted so as to lie between the first upstream portion 1Aa and the first downstream portion 1Ab of the intermediate cover member 1A via the metallic thin wire 27. Note that either of the intermediate cover member 1A and the detection element 3 may be the first to be placed on the first cover member 1.

Next, as shown in FIG. 9(d), the filler member 9 is placed in a gap between the detection element 3 and the intermediate cover member 1A.

Next, as shown in FIG. 9(e), the third substrate 2a of the second cover member 2 is laminated onto the intermediate cover member 1A.

Then, as shown in FIG. 9(a), the fourth substrate 2b is laminated onto the third substrate 2a, whereupon the sensor apparatus 101 in accordance with the present embodiment is produced.

Modified Example 4

Figure 10:
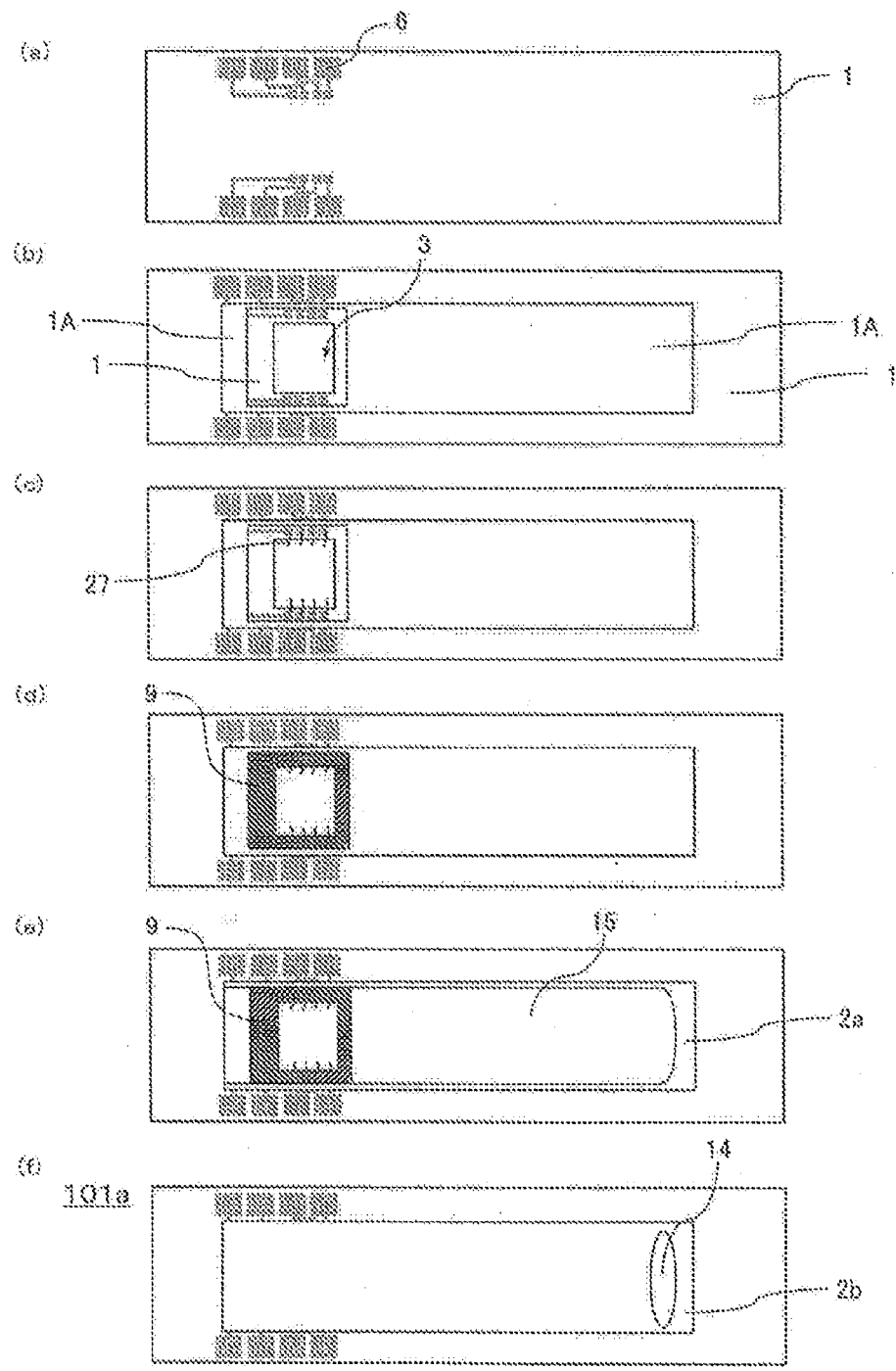
FIG. 10 is a view showing a modified example of the sensor apparatus shown in FIG. 1, particularly illustrating manufacturing steps.

FIG. 10 is a view of a sensor apparatus 101a which is a modified example of the sensor apparatus 100 shown in FIG. 1, particularly illustrating manufacturing steps.

In contrast to the sensor apparatus 100 of the foregoing first embodiment, in the sensor apparatus 101a of this modified example, in a top view, the detection element 3 is surrounded throughout its periphery by the intermediate cover member 1A. Moreover, as shown in FIGS. 10(d) and 10(e), the filler member 9 is disposed in a gap between the detection element 3 and the intermediate cover member 1A so as to surround the outer edge of the detection element 3. This makes it possible to reduce the difference in level or a gap between the detection element 3 and a nearby area in the flow channel 15, and thereby allow an analyte liquid to flow smoothly over the detection element 3. Moreover, in a region between the detection element 3 and the terminals 6, the filler member 9 covers part of the wiring lines 7 and also a lead wire 27 for providing connection between the detection element 3 and the wiring line 7, thus reducing a decrease in detection sensitivity caused by a contact between these constituent components and an analyte liquid.

In this modified example, after the formation of the intermediate cover member 1A and the detection element 3 as shown in FIG. 10(b), the detection element 3 and the wiring line 7 are connected to each other via the lead wire 27 as shown in FIG. 10(c). As an alternative, after the formation of the detection element 3 and the subsequent process of connecting the detection element 3 with the wiring line 7 via the lead wire 27, the intermediate cover member 1A is formed.

Modified Example 5

Figure 11:
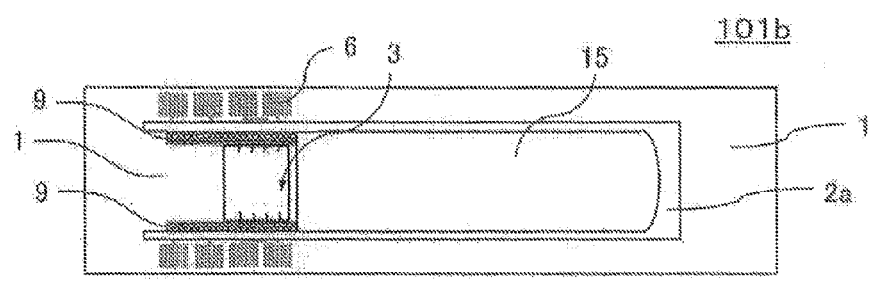
FIG. 11 is a plan view showing a modified example of the sensor apparatus shown in FIG. 1, which corresponds to FIG. 5(d)
Figure 11:
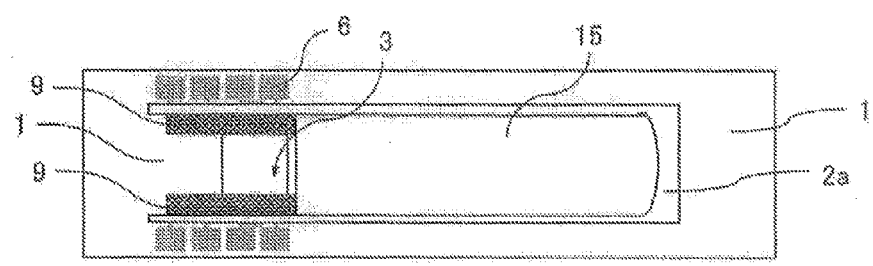

FIG. 11 is a plan view showing sensor apparatuses 101b and 101c which are each a modified example of the sensor apparatus 100 shown in FIG. 1, and, which corresponds to FIG. 5(d).

In contrast to the sensor apparatus 100 of the foregoing first embodiment, in the sensor apparatuses 101b and 101c of this modified example, as shown in FIGS. 11(a) and 11(b), the filler member 9 is disposed in part of a gap between the detection element 3 and the intermediate cover member 1A which extends in the direction of the length of the flow channel 15. This makes it possible to reduce the difference in level or a gap between the detection element 3 and the area on each side of the detection element 3, and thereby allow an analyte liquid to smoothly flow sideways in relation to the detection element 3. Moreover, in the region between the detection element 3 and the terminals 6, the filler member 9 covers part of the wiring lines 7 and also the lead wire 27 for providing connection between the detection element 3 and the wiring line 7, thus reducing a decrease in detection sensitivity caused by a contact between these constituent components and an analyte liquid.

Moreover, as shown in FIG. 11(b), the filler member 9 may be disposed so as to cover not only the gap between the detection element 3 and the intermediate cover member 1A but also part of the lead wire 27 for providing connection between the detection element 3 and the wiring line 7 which lies on the upper surface of the detection element 3 (element substrate 10). This makes it possible to achieve further reduction of a decrease in detection sensitivity caused by a contact between the lead wire 27 and an analyte liquid.

In the sensor apparatus 100 of the first embodiment and the sensor apparatuses which are each a modified example of the sensor apparatus 100 thus far described, the configuration of a sensor apparatus of each of the following embodiments is applicable as it is or in a form adapted to the aforestated constructions.

Second Embodiment

Figure 12:
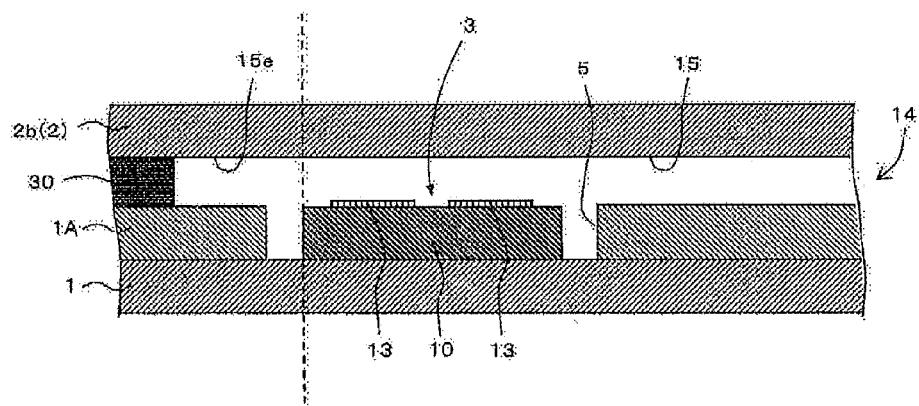
FIG. 12 is a view showing a sensor apparatus in accordance with a second embodiment of the invention, and, this figure corresponds to FIG. 2(a)

FIG. 12 is a view showing a sensor apparatus 200 in accordance with a second embodiment of the invention, which corresponds to FIG. 2(a).

In the sensor apparatus 200 of this embodiment, a liquid absorbing material 30 which absorbs an analyte liquid at a predetermined rate is located at the terminal end of the flow channel 15 on the upper surface of the first downstream portion 1Ab of the intermediate cover member 1A. In this case, an excess of the analyte liquid is absorbed, thus enabling the flow of a uniform amount of the analyte liquid over the detection section 13, wherefore measurement can be effected with high stability. As the liquid absorbing material 30, use can be made of a porous material such as a sponge capable of liquid absorption, and more specifically, for example, nitrocellulose is desirable for use.

Also in the sensor apparatus 200 of this embodiment, like the sensor apparatus 100 of the foregoing first embodiment, the detection element 3 and the intermediate cover member 1A which constitutes at least part of the flow channel are juxtaposed on the upper surface of the first cover member 1. Thus, even with use of the detection element 3 having a certain thickness, an analyte liquid flow channel extending from the inflow section to the detection section can be provided, wherefore the analyte liquid sucked through the inflow section under capillarity, for example, can be delivered to the detection section. That is, there is provided the sensor apparatus 200 which incorporates the detection element 3 having a certain thickness and yet includes an analyte liquid suction mechanism built in itself, and is thus capable of measurement operation in a simple way. Moreover, in the analyte liquid flow channel, the contact angle $\theta 1a$, $\theta 2a$ of the surface of the member located upstream of the detection element 3 with an analyte liquid is smaller than the contact angle $\theta 3$ of the surface of the detection element 3 with an analyte liquid, thus enabling the analyte liquid which has flowed into the flow channel from the inflow section to flow smoothly to the detection element 3 (detection section 13) over the surface of the member located on the upstream side.

Moreover, in this embodiment, the contact angle $\theta 1b$ of the upper surface of the first downstream portion 1Ab of the intermediate cover member 1A with an analyte liquid may be set to be greater than the contact angle $\theta 3$. This makes it possible to adjust the speed at which the analyte liquid which has passed through the detection element 3 (detection section 13) is absorbed by the liquid absorbing material 30, and thereby exercise control so that the amount of the analyte liquid over the detection element 3 (detection section 13) stands at a predetermined level, thus achieving an improvement in detection stability.

Next, modified examples of the sensor apparatus 200 of the second embodiment will be described.

Modified Example

Modified Example 6

Figure 13:
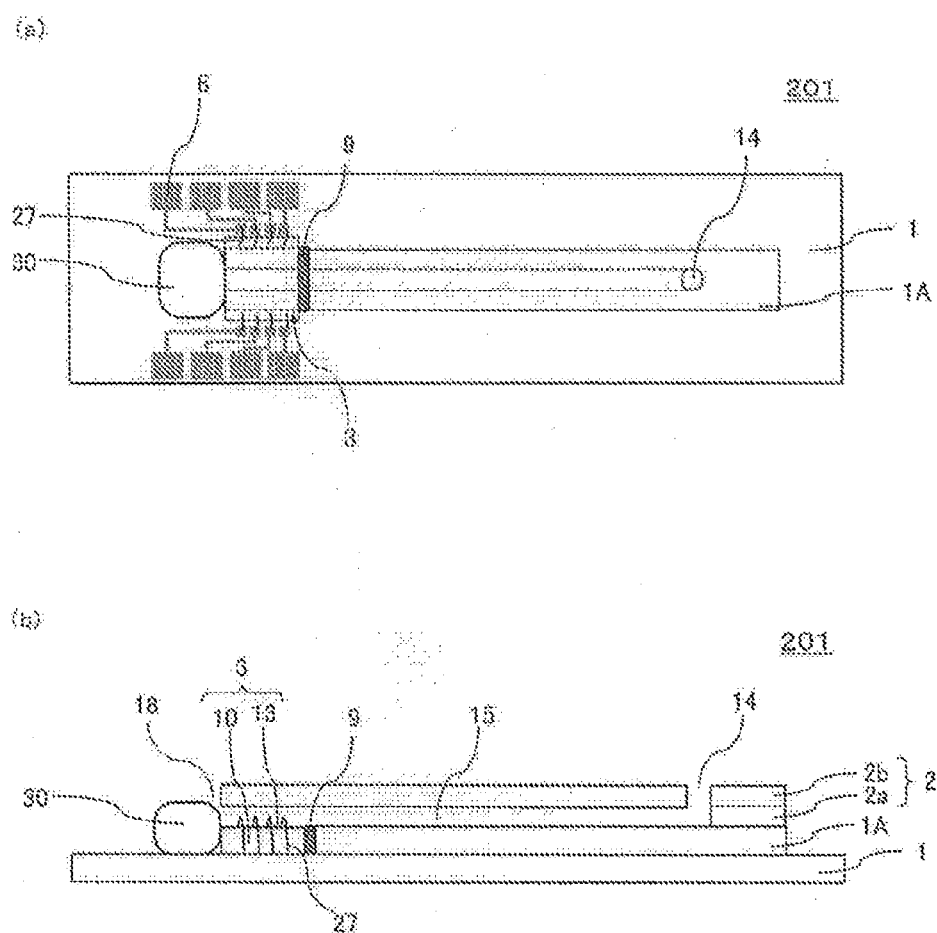
FIG. 13 is a view showing a modified example of the sensor apparatus shown in FIG. 12.

FIG. 13 is a view showing a sensor apparatus 201 which is a modified example of the sensor apparatus 200 shown in FIG. 12, and FIG. 13(a) is a plan view and FIG. 13(b) is a lengthwise sectional view.

In the sensor apparatus 201 of this modified example, instead of the first downstream portion 1Ab of the intermediate cover member 1A of the sensor apparatus 100 of the foregoing first embodiment, a liquid absorbing material 30 is located at a position on the upper surface of the first cover member 1, the position being on the opposite side of the detection element 3 from the intermediate cover member 1A. Also in this modified example, an excess of the analyte liquid is absorbed, thus enabling the flow of a uniform amount of the analyte liquid over the detection section 13, wherefore measurement can be effected with high stability.

In this modified example, the liquid absorbing material 30 is spaced slightly away from the terminal end of the flow channel 15. In this case, the gap serves as the exhaust hole 18, thus achieving effective exploitation of capillarity.

Modified Example 7

Figure 14:
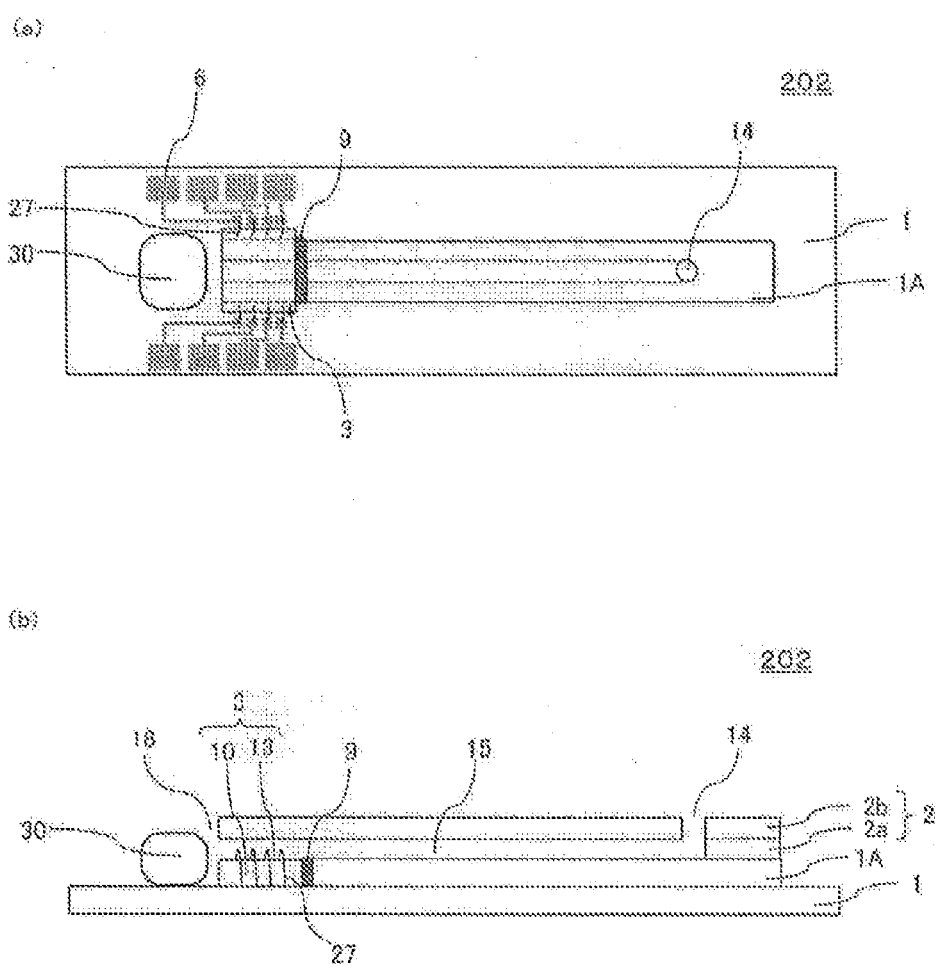
FIG. 14 is a view showing a modified example of the sensor apparatus shown in FIG. 12.

FIG. 14 is a view showing a sensor apparatus 202 which is a modified example of the sensor apparatus 200 shown in FIG. 12, and FIG. 14(a) is a plan view and FIG. 14(b) is a lengthwise sectional view.

In contrast to the sensor apparatus 201 shown in FIG. 13, in the sensor apparatus 202 of this modified example, as shown in FIG. 14, the liquid absorbing material 30 is placed on the upper surface of the first cover member 1 so as to lie on the opposite side of the detection element 3 from the intermediate cover member 1A, with a gap left between the liquid absorbing material 30 and the detection element 3. In this case, an analyte liquid flowing through the flow channel 15 is absorbed by the liquid absorbing material 30 after passing over the upper surface of the detection element 3, wherefore it is possible to absorb the analyte liquid which has already completed contribution to detection on the upper surface of the detection element 3.

Modified Example 8

Figure 15:
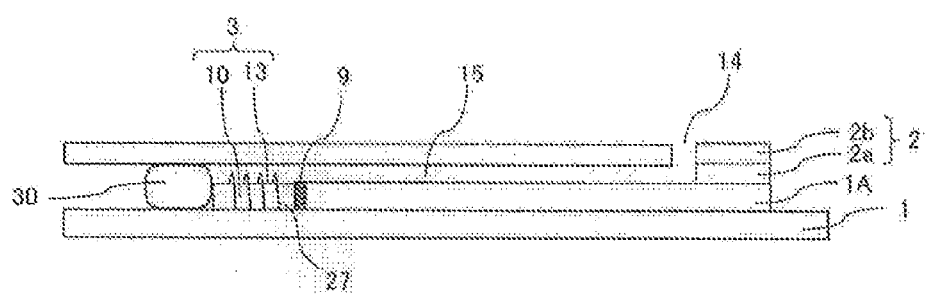
FIG. 15 is a lengthwise sectional view showing a modified example of the sensor apparatus shown in FIG. 12.
Figure 15:
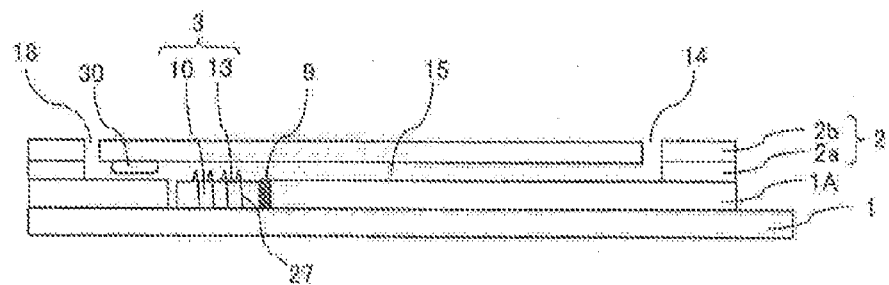

FIG. 15 is a sectional view showing sensor apparatuses 203 and 204 lengthwise, which are each a modified example of the sensor apparatus 200 shown in FIG. 12.

In contrast to the sensor apparatus 201 shown in FIG. 13, in the sensor apparatus 203 of this modified example, as shown in FIG. 15(a), the liquid absorbing material 30 contacts with both of the upper surface of the first cover member 1 and the lower surface of the second cover member 2, namely the upper and lower surfaces of the flow channel 15. In this case, as described previously, an excess of the analyte liquid is absorbed, thus enabling the flow of a uniform amount of the analyte liquid over the detection section 13, wherefore measurement can be effected with high stability.

Moreover, in this modified example, with adjustment of the porosity of the liquid absorbing material 30, the porous liquid absorbing material 30 serves also as the exhaust hole 18. In this case, by placing the liquid absorbing material 30 so as to contact with not only the upper and lower surfaces of the flow channel 15 as above described but also the side wall of the flow channel 15, it is possible to dispose the liquid absorbing material 30 so as to block the flow channel 15.

Moreover, in contrast to the sensor apparatus 201 shown in FIG. 13, in the sensor apparatus 204 of another modified example, as shown in FIG. 15(b), the liquid absorbing material 30 contacts only with the upper surface of the first cover member 1. In this case, the liquid absorbing material 30 enables analyte liquid attraction upon contact with an analyte liquid flowing through the flow channel 15, for example. Thus, it is possible to effectively guide the analyte liquid toward the upper surface of the detection element 3 located forward in an analyte liquid traveling direction.

In contrast to the sensor apparatus 100 of the first embodiment, in the sensor apparatus 204, the fourth substrate 2b is provided with an exhaust hole 18 which passes therethrough in its thickness direction. The exhaust hole 18 is located so as to be continuous with the end of the flow channel 15.

The invention is not limited to the aforestated embodiments, and may therefore be carried into effect in various forms.

While, in the aforestated embodiments, there is illustrated the detection section 13 comprising a metal film and an aptamer immobilized on the surface of the metal film, for example, in a case where a target contained in an analyte liquid reacts with the metal film, the detection section 13 may be composed solely of the metal film without using an aptamer. Further, the detection section 13 may be defined by a region between the first IDT electrode 11 and the second IDT electrode 12 on the surface of the element substrate 10 constructed of a piezoelectric substrate without using a metal film. In this case, an analyte liquid is applied directly to the surface of the element substrate 10 to detect the physical properties, such as the viscosity, of the analyte liquid. More specifically, phase variation in SAW entailed by, for example, changes of the viscosity of the analyte liquid on the detection section 13 is measured. Moreover, an aptamer may be immobilized on the surface of a non-conductive film instead of a metal film.

Moreover, while, in the aforestated embodiments, there is illustrated the detection element 3 comprising a surface acoustic wave element, the detection element 3 is not limited to this, and thus use can be made of, for example, a detection element 3 provided with an optical waveguide or the like for induction of surface plasmon resonance. In this case, for example, variation in optical refractive index in the detection section is measured. In addition, use can be made of a detection element 3 constructed of a piezoelectric substrate, such as a quartz substrate, provided with an oscillator. In this case, for example, variation in oscillation frequency in the oscillator is measured.

Moreover, a construction comprising a plurality of different devices disposed on a single substrate may be adopted as the detection element 3. For example, an enzyme electrode for use with the enzyme electrode method may be disposed next to a SAW element. In this case, in addition to measurement based on the immunization method using an antibody or aptamer, measurement based on the enzymatic method can be conducted, thus increasing the number of measurement points that can be checked at one time.

Moreover, while, in the aforestated embodiments, there is illustrated the construction comprising a single detection element 3, a plurality of detection elements 3 may be provided. In this case, the element receiving recess 5 may be provided for each detection element 3 on an individual basis, or alternatively the element receiving recess 5 may be configured to have a length or width large enough to receive all of the detection elements 3.

Moreover, while, in the aforestated embodiments, there are illustrated the first cover member 1, the intermediate cover member 1A, and the second cover member 2 which are provided as separate components, this does not constitute any limitation, and thus a combination of two of these members in an unitary structure may be adopted. Alternatively, a combination of all the members in an unitary structure may be adopted.

Moreover, the configuration of each modified example of the sensor apparatus 100 of the first embodiment may be applied to the sensor apparatus 200 of the second embodiment. That is, the modified examples and the forms of the constituent components related to the sensor apparatus of a certain embodiment described hereinabove may be applied to the sensor apparatus of another embodiment without departing from the technical concept of the invention.

REFERENCE SIGNS LIST

1: First cover member
1A: Intermediate cover member
1Aa: First upstream portion
θ1a: Contact angle
1Ab: First downstream portion
θ1b: Contact angle
2: Second cover member
2a: Third substrate
2b: Fourth substrate
2ba: Second upstream portion
θ2a: Contact angle 2bb: Second downstream portion
θ2b: Contact angle
3: Detection element
3a: Upstream region
θ3a: Contact angle
3b: Detection region (Detection section)
θ3b: Contact angle
3c: Downstream region
θ3c: Contact angle
4: Recess-forming area
5: Element receiving recess
6: Terminal
7: Wiring line
9: Filler member
10: Element substrate
11: First IDT electrode
12: Second IDT electrode
13(13b): Detection section
14: Inflow section
15: Flow channel
15a: Upstream part
15b: Downstream part (extension)
18: Exhaust hole
19: First extraction electrode
19e: End
20: Second extraction electrode
20e: End
27: Lead wire (metallic thin wire)
28: Insulating member
30: Liquid absorbing material

The invention claimed is:

1. A sensor apparatus, comprising:
an inflow section into which an analyte liquid flows;
a first cover member;
a detection element comprising an element substrate located on an upper surface of the first cover member, and a detection section which is located on an upper surface of the element substrate and is configured to detect a target contained in an analyte liquid;
an intermediate cover member comprising a first upstream portion which is located on the upper surface of the first cover member and is located on a side of the inflow section with respect to the detection element;
a second cover member which covers the detection element, joins to at least one of the first cover member and the intermediate cover member, and comprises a second upstream portion located on a side of the inflow section with respect to the detection element; and
a flow channel which is surrounded by the intermediate cover member and the second cover member, is continuous with the inflow section, and extends at least to the detection section,
wherein a contact angle $\theta 2a$ of a lower surface of the second upstream portion of the second cover member with the analyte liquid is smaller than a contact angle $\theta 3$ of an upper surface of the detection element with the analyte liquid.

2. A sensor apparatus, comprising:
an inflow section into which an analyte liquid flows;
a first cover member;
a detection element comprising an element substrate located on an upper surface of the first cover member, and a detection section which is located on an upper surface of the element substrate and is configured to detect a target contained in an analyte liquid;
an intermediate cover member comprising a first upstream portion which is located on the upper surface of the first cover member and is located on a side of the inflow section with respect to the detection element;
a second cover member which covers the detection element, joins to at least one of the first cover member and the intermediate cover member, and comprises a second upstream portion located on a side of the inflow section with respect to the detection element; and
a flow channel which is surrounded by the intermediate cover member and the second cover member, is continuous with the inflow section, and extends at least to the detection section,
wherein a contact angle $\theta 1a$ of an upper surface of the first upstream portion of the intermediate cover member with the analyte liquid is smaller than a contact angle $\theta 3$ of an upper surface of the detection element with the analyte liquid.

3. The sensor apparatus according to claim 1,
wherein a contact angle $\theta 2a$ of the lower surface of the second upstream portion of the second cover member with the analyte liquid is equal to or smaller than a contact angle $\theta 1a$ of an upper surface of the first upstream portion of the intermediate cover member with the analyte liquid.

4. The sensor apparatus according to claim 1, wherein
the intermediate cover member further comprises a first downstream portion located away from the inflow section beyond the detection element, and
a contact angle $\theta 1b$ of an upper surface of the first downstream portion with the analyte liquid is greater than the contact angle $\theta 1a$.

5. The sensor apparatus according to claim 1, wherein
the second cover member further comprises a second downstream portion located away from the inflow section beyond the detection element, and
a contact angle $\theta 2b$ of an upper surface of the second downstream portion with the analyte liquid is greater than the contact angle $\theta 2a$.

6. The sensor apparatus according to claim 1, wherein
the upper surface of the detection element comprises an upstream region located upstream of the detection section in the flow channel, and
a contact angle $\theta 3a$ of the upstream region with the analyte liquid is smaller than a contact angle $\theta 3b$ of the detection section with the analyte liquid.

7. The sensor apparatus according to claim 1, wherein
the upper surface of the detection element further comprises a downstream region located downstream of the detection section in the flow channel, and
a contact angle $\theta 3c$ of the downstream region with the analyte liquid is smaller than a contact angle $\theta 3b$ of the detection section with the analyte liquid.

8. The sensor apparatus according to claim 7,
wherein the contact angle $\theta 3a$ is smaller than the contact angle $\theta 3c$.

9. The sensor apparatus according to claim 1,
wherein a level of an upper surface of the first upstream portion of the intermediate cover member is equal to or higher than a level of the upper surface of the detection element.

10. The sensor apparatus according to claim 1, wherein
the first cover member is shaped like a flat plate, and
the first upstream portion of the intermediate cover member is greater in thickness than the detection element.

11. The sensor apparatus according to claim 1, further comprising:

a liquid absorbing material located at a position on the upper surface of the first cover member, the position being located away from the inflow section beyond the detection element.

12. The sensor apparatus according to claim 11, wherein the intermediate cover member further comprises a first downstream portion located away from the inflow section beyond the detection element, and a contact angle $\theta 1b$ of an upper surface of the first downstream portion with the analyte liquid is greater than the contact angle $\theta 3$.

13. The sensor apparatus according to claim 1, wherein the detection element and the intermediate cover member are located with a gap on the upper surface of the first cover member.

14. The sensor apparatus according to claim 13, further comprising:

a filler member disposed in the gap between the detection element and the intermediate cover member.

15. The sensor apparatus according to claim 1, wherein the detection element is surrounded by the intermediate cover member as seen in a top view.

16. The sensor apparatus according to claim 1, wherein the flow channel is surrounded by the first cover member, the intermediate cover member, and the second cover member.

17. The sensor apparatus according to claim 1, wherein the inflow section is configured to pass through the second cover member in a thickness direction thereof.

* * * * *